US006572576B2

(12) United States Patent
Brugger et al.

(10) Patent No.: US 6,572,576 B2
(45) Date of Patent: Jun. 3, 2003

(54) METHOD AND APPARATUS FOR LEAK DETECTION IN A FLUID LINE

(75) Inventors: James M. Brugger, Newburyport, MA (US); Jeffrey H. Burbank, Boxford, MA (US); Dennis M. Treu, Bedford, NH (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 09/900,362

(22) Filed: Jul. 7, 2001

(65) Prior Publication Data

US 2003/0009123 A1 Jan. 9, 2003

(51) Int. Cl.$^7$ .................. A61M 37/00; A61M 1/00; C02F 1/44; C02F 1/00; B01D 35/00; B01D 35/14; B01D 35/147; B01D 11/00; B01D 61/00

(52) U.S. Cl. .................. 604/4.01; 604/118; 604/122; 604/149; 210/90; 210/646; 210/739; 210/741

(58) Field of Search .................. 604/4.01, 122, 604/149, 118; 210/90, 646, 739, 741

(56) References Cited

U.S. PATENT DOCUMENTS 3,648,694 A * 3/1972 Mogos et al. .............. 604/118
5,690,831 A * 11/1997 Kenley et al. .............. 210/646
6,284,142 B1 * 9/2001 Muller ....................... 210/745

OTHER PUBLICATIONS

Ellingboe et al., Blood Perfusion System, Jul. 4, 2002.*
Burbank et al., Systems and Methods for Performing Blood Processing and/or Fluid Exchange Procedures, Oct. 10, 2002.*

* cited by examiner

Primary Examiner—William C. Doerrler
Assistant Examiner—Filip Zec
(74) Attorney, Agent, or Firm—Proskauer Rose LLP

(57) ABSTRACT

One of the most significant safety concerns in the automation of extracorporeal blood treatments such as dialysis is the risk of blood leakage. Such systems draw blood at such a high rate that a loss of integrity in the blood circuit can be catastrophic. The most reliable leak detection method known is the detection of infiltrated air in a blood line, but this only works in blood lines under negative pressure. According to the invention, a leak detector for return lines is provided by periodically generating a negative pressure, which may be brief or at a 50% duty cycle, in the blood return line to draw air into it and thereby reveal the leaks using an air sensor. Although the return line is ordinarily under positive pressure, during the negative pressure cycle, the blood return line draws air through any leaks or disconnects. If air is detected, the system is shut down and an alarm generated.

89 Claims, 13 Drawing Sheets

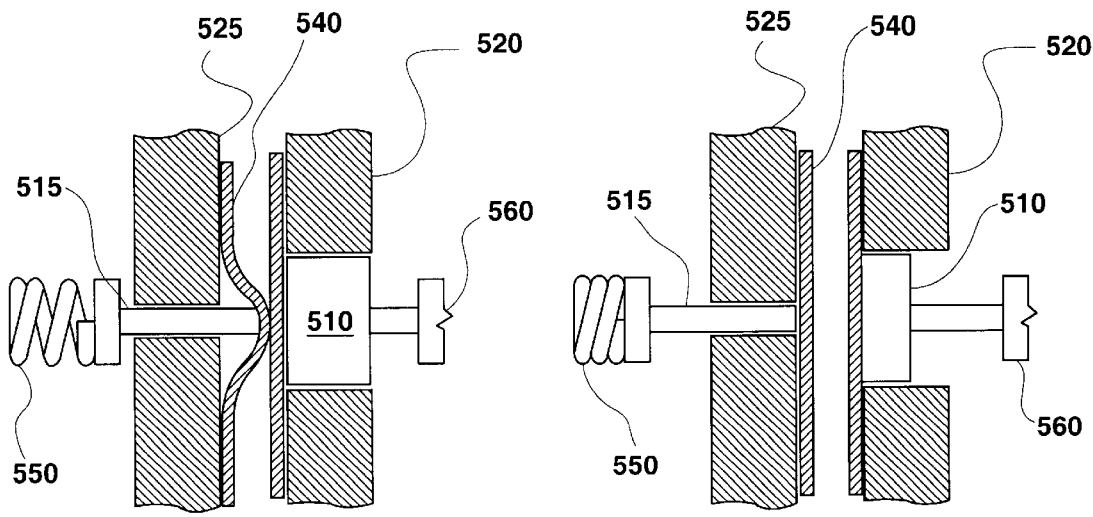
Fig. 11 A
Fig. 11C
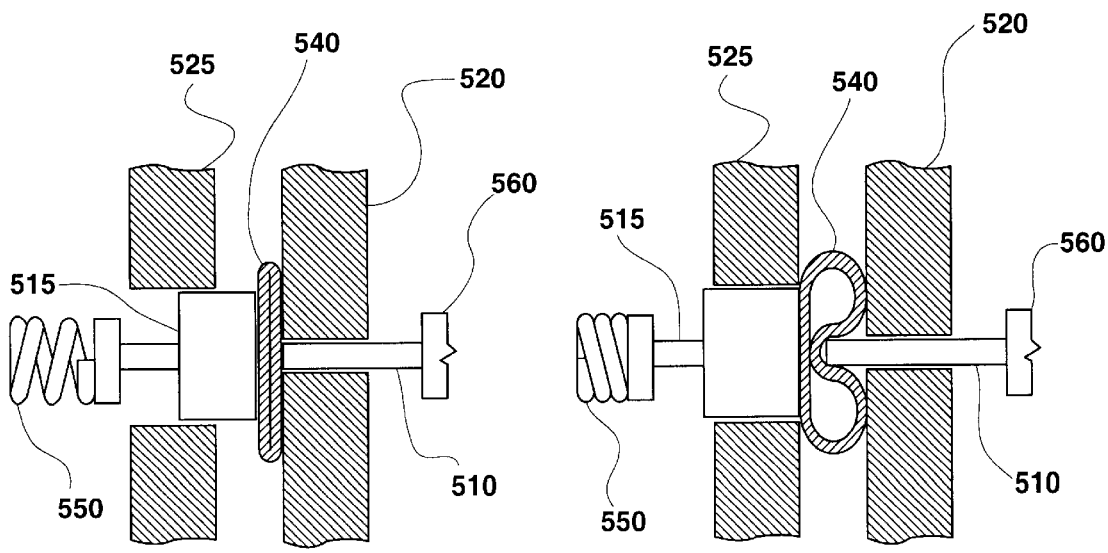
Fig. 11B
Fig. 11 D

METHOD AND APPARATUS FOR LEAK DETECTION IN A FLUID LINE

FIELD OF THE INVENTION

The present invention relates to the detection of leaks (including needle-disconnects and other causes of loss of integrity) in extracorporeal blood circuits and more particularly to the application of air infiltration detection techniques to the detection of leaks in positive pressure return lines.

BACKGROUND

Many medical procedures involve the extraction and replacement of flowing blood from, and back into, a donor or patient. The reasons for doing this vary, but generally, they involve subjecting the blood to some process that cannot be carried out inside the body. When the blood is outside the patient it is conducted through machinery that processes the blood. The various processes include, but are not limited to, hemodialysis, hemofiltration, hemodiafiltration, blood and blood component collection, plasmaphresis, aphresis, and blood oxygenation.

One technique for extracorporeal blood processing employs a single "access," for example a single needle in the vein of the patient or a fistula. A volume of blood is cyclically drawn through the access at one time, processed, and then returned through the same access at another time. Single access systems are uncommon because they limit the rate of processing to half the capacity permitted by the access. As a result, two-access systems, in which blood is drawn from a first access, called an arterial access, and returned through a second access, called a venous access, are much faster and more common. These accesses include catheters, catheters with subcutaneous ports, fistulas, and grafts.

The processes listed above, and others, often involve the movement of large amounts of blood at a very high rate. For example, 500 ml. of blood may be drawn out and replaced every minute, which is about 5% of the patient's entire supply. If a leak occurs in such a system, the patient could be drained of enough blood in a few minutes to cause loss of consciousness with death following soon thereafter. As a result, such extracorporeal blood circuits are normally used in very safe environments, such as hospitals and treatment centers, and attended by highly trained technicians and doctors nearby. Even with close supervision, a number of deaths occur in the United States every year due to undue blood loss from leaks.

Leaks present a very real risk. Leaks can occur for various reasons, among them: extraction of a needle, disconnection of a luer, poor manufacture of components, cuts in tubing, and leaks in a catheter. However, in terms of current technology, the most reliable solution to this risk, that of direct and constant trained supervision in a safe environment, has an enormous negative impact on the lifestyles of patients who require frequent treatment and on labor requirements of the institutions performing such therapies. Thus, there is a perennial need in the art for ultra-safe systems that can be used in a non-clinical setting and/or without the need for highly trained and expensive staff. Currently, there is great interest in ways of providing systems for patients to use at home. One of the risks for such systems is the danger of leaks. As a result, a number of companies have dedicated resources to the solution of the problem of leak detection.

In single-access systems, loss of blood through the patient access and blood circuit can be indirectly detected by detecting the infiltration of air during the draw cycle. Air is typically detected using an ultrasonic air detector on the tubing line, which detects air bubbles in the blood. The detection of air bubbles triggers the system to halt the pump and clamp the line to prevent air bubbles from being injected into the patient. Examples of such systems are described in U.S. Pat. Nos. 3,985,134, 4,614,590, and 5,120,303.

While detection of air infiltration is a reliable technique for detecting leaks in single access systems, the more attractive two-access systems, in which blood is drawn continuously from one access and returned continuously through another, present problems. While a disconnection or leak in the draw line can be sensed by detecting air infiltration, just as with the single needle system, a leak in the return line cannot be so detected. This problem has been addressed in a number of different ways, some of which are generally accepted in the industry.

The first level of protection against return line blood loss is the use of locking luers on all connections, as described in International Standard ISO 594-2 which help to minimize the possibility of spontaneous disconnection during treatment. Care in the connection and taping of lines to the patient's bodies is also a known strategy for minimizing this risk.

A higher level of protection is the provision of venous pressure monitoring, which detects a precipitous decrease in the venous line pressure. This technique is outlined in International Standard IEC 60601-2-16. This approach, although providing some additional protection, is not very robust, because most of the pressure loss in the venous line is in the needle used to access the patient. There is very little pressure change in the venous return line that can be detected in the event of a disconnection, so long as the needle remains attached to the return line. Thus, the pressure signal is very weak. The signal is no stronger for small leaks in the return line, where the pressure changes are too small to be detected with any reliability. One way to compensate for the low pressure signal is to make the system more sensitive, as described in U.S. Pat. No. 6,221,040, but this strategy can cause many false positives. It is inevitable that the sensitivity of the system will have to be traded against the burden of monitoring false alarms. Inevitably this leads to compromises in safety. In addition, pressure sensing methods cannot be used at all for detecting small leaks.

Yet another approach, described for example in PCT application US98/19266, is to place fluid detectors near the patient's access and/or on the floor under the patient. The system responds only after blood has leaked and collected in the vicinity of a fluid detector. A misplaced detector can defeat such a system and the path of a leak cannot be reliably predicted. For instance, a rivulet of blood may adhere to the patient's body and transfer blood to points remote from the detector. Even efforts to avoid this situation can be defeated by movement of the patient, deliberate or inadvertent (e.g., the unconscious movement of a sleeping patient).

Still another device for detecting leaks is described in U.S. Pat. No. 6,044,691. According to the description, the circuit is checked for leaks prior to the treatment operation. For example, a heated fluid may be run through the circuit and its leakage detected by means of a thermistor. The weakness of this approach is immediately apparent: there is no assurance that the system's integrity will persist, throughout the treatment cycle, as confirmed by the pre-treatment test. Thus, this method also fails to address the entire risk.

Yet another device for checking for leaks in return lines is described in U.S. Pat. No. 6,090,048. In the disclosed system, a pressure signal is sensed at the access and used to infer its integrity. The pressure wave may be the patient's pulse or it may be artificially generated by the pump. This approach cannot detect small leaks and is not very sensitive unless powerful pressure waves are used, in which case the effect can produce considerable discomfort in the patient.

Clearly detection of leaks by prior art methods fails to reduce the risk of dangerous blood loss to an acceptable level. In general, the risk of leakage-related deaths increases with the decrease in medical staff per patient driven by the high cost of trained staff. Currently, with lower staffing levels comes the increased risk of unattended leaks. Thus, there has been, and continues to be, a need in the prior art for a foolproof approach to detection of a return line leak or disconnection.

In an area unrelated to leak detection, U.S. Pat. No. 6,177,049 B1 suggests the idea of reversing the direction of blood flow for purposes of patency testing and access-clearing. The patency tests alluded to by the '049 patent refer simply to the conventional idea of forcing blood through each access to clear occlusions and to ascertain the flow inside a fistula.

SUMMARY OF THE INVENTION

Leaks in the arterial portion of a two-access extracorporeal blood circuit can be very reliably detected because the arterial access line is generally under negative pressure. Thus, any loss of integrity of the arterial circuit—at least those parts under negative pressure—will result in the infiltration of air into the circuit, which can then be detected by an ultrasonic air bubble detector. The air bubble detector is so reliable that, since its introduction in the 1970's no deaths have been attributed to the failure of this technology to detect a leak. According to the invention, the same technique can be applied to the physical parts of the circuit that are ordinarily under positive pressure by intermittently subjecting them to negative pressure throughout treatment. That is, periodically, the venous side of the circuit is subjected to a negative pressure thereby causing air to infiltrate through any openings in the circuit such as caused by a leak, a loose needle, or a disconnected luer. A conventional air detector, such as an ultrasonic detector, may then be relied upon to detect the loss of integrity and an appropriate response generated. Other technologies, such as radio frequency detection technology, direct audio detection of infiltration using a hydrophone, and others may also be used.

In an embodiment of the invention, the flow of blood from the arterial access to the venous access is periodically reversed. This causes a negative pressure in the venous part of the circuit which, if compromised by a loose or extracted needle or leak, will result in detectable air infiltration. The air infiltration may be detected by the same means used for detecting leaks in the arterial part of the circuit. Advantageously, the flow reversal technique can allow the same leak detection device to be used for detecting both venous circuit leaks and arterial circuit leaks, as long as the flow of blood is controlled in such a way as to insure that any resulting bubbles arrive at the air detector.

To insure that leaks are detected early enough to avoid harm, the period of the flow reversal cycles may be made no greater than a ratio of the maximum allowable blood volume loss to the volume flow rate of the blood. Note that in determining this quantity, due consideration should be given to the fact that some of the patient's blood is already outside of his/her body in the circuit of the machine. Thus, if the maximum blood loss a patient can tolerate is 500 ml. and the rate of flow of blood is 500 ml./min., the period of the flow reversal cycles may be made no greater than one minute to insure a high level of security.

One technique for reversing the flow in a two-access circuit is to reverse the pump. Another technique is to provide separate pumps, one for each flow direction. At each moment only one pump would run, while the idle pump would either block flow if plumbed as a parallel circuit, or permit flow (e.g., a bypass), if plumbed as a series circuit.

Another technique for providing flow reversal is to employ a four-way valve, which is a four-port valve that transposes the interconnections between the inputs and outputs of the pump and those of the venous and arterial circuits, respectively. Examples of four-way valves that may be used to accomplish this are described in U.S. Pat. Nos. 5,894,011, 5,605,630, 6,177,049, 4,885,087, 5,830,365, and 6,189,388. These prior art valves, however, either suffer from being non-hermetic so that they have seals; are intended to be reused; have stagnant zones, or are simply too expensive.

Preferably, in an ideal four-way valve, the wetted parts form a part of a hermetic disposable unit and have no dead spaces where blood could stagnate. According to an embodiment of the invention, a preferred configuration of a four-way valve defines an H-shaped bridge that is alternately pinched by respective perpendicular anvil-edges to form alternate flow configurations. To form the first configuration, a first anvil-edge pinches the H-shaped bridge at the center of the crossing line of the "H" to form mirror image U-shaped channels. In the second configuration, a second anvil edge, perpendicular to the first, pinches the bridge to bisect it and form two parallel channels. Various other hermetic configurations are possible, preferably each provides a four-way valve function and no dead (i.e., no-flow) spaces, which could cause clotting or other deleterious effects, within the valve.

According to another embodiment of the invention, negative pressure in the venous line is generated in just the return circuit. This may be done by periodic paroxysmal expansion of a bladder plumbed inline in the venous circuit. The sudden expansion generates a negative pressure in the venous circuit, drawing air into the blood and exposing any loss of integrity via an appropriately-located air infiltration detector.

The invention will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

FIG. 11A is a side view of a mechanism for actuating the valves of FIGS. 9A–9C and 10A–10C in a first position.

FIG. 11B is a top view of the mechanism for actuating the valves of FIGS. 9A–9C and 10A–10C in the first position of FIG. 11A.

FIG. 11C is a side view of the mechanism for actuating the valves of FIGS. 9A–9C and 10A–10C in a second position.

FIG. 11D is a top view of the mechanism for actuating the valves of FIGS. 9A–9C and 10A–10C in the second position of FIG. 11C.

DETAILED DESCRIPTION OF THE EMBODIMENTS

Figure 1:
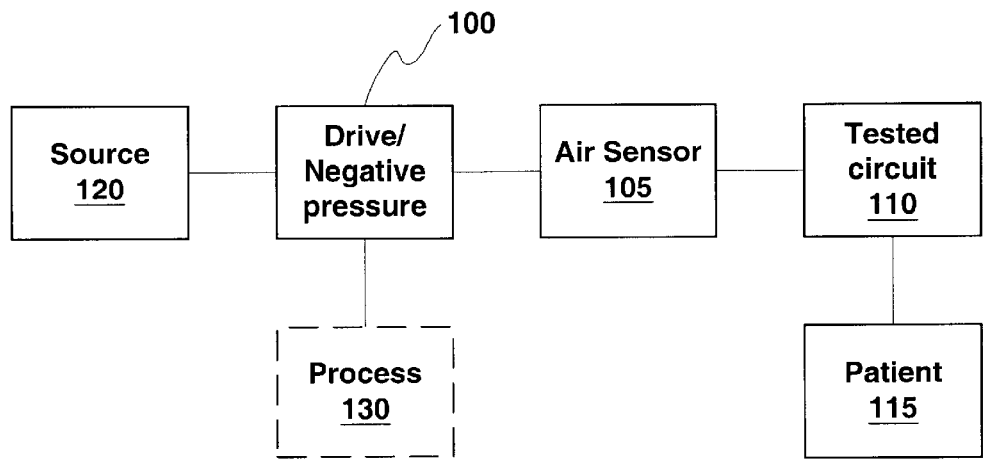
FIG. 1 is a figurative illustration of a blood circuit leak detector during a return operation according to an embodiment of the invention.

Referring to FIG. 1, elements of an embodiment of the invention are illustrated schematically. A source of fluid 120 (for example blood) supplies fluid to a drive/negative pressure device 100 that does at least two things: it moves the fluid to the patient and it selectively generates negative pressure. It may also incorporate, or be connected with, a treatment process 130, for example a hemofiltration, hemodialysis, hemodiafiltration, or other blood treatment process. A fluid circuit connects the drive/negative pressure device 100 to an air sensor 105, which is in turn connected to a tested fluid circuit 110 whose leak-integrity must be assured. Finally, fluid is introduced into a patient 115. Note that in some embodiments, the drive/negative pressure device 100 may be transposed with the air sensor 105, as long as it is assured that any leaks in the tested circuit 110 will arrive at at least one air sensor. Air sensors may be arranged in the tested circuit as well.

The source of fluid 120 is most likely blood from the patient 115, as would be the case for an extracorporeal blood treatment process such as hemofiltration or dialysis. That is, the circuit 120, 100, 105, 110, may be a two-access draw/return circuit with some sort of treatment process 130 connected with it. However, the source of fluid could also be a storage vessel in a single access circuit or a quantity of blood being transfused or infused. The essential feature of the circuit of FIG. 1 is that it is a supply circuit generally introducing fluid to the patient 115.

The air sensor 105 detects air bubbles in the tested circuit when the flow of fluid is reversed in at least a portion of the tested circuit 110 by the inducement of negative pressure in the tested circuit 110 by the drive/negative pressure device 100. The tested circuit 110 may include any part of an extracorporeal treatment circuit where there is ordinarily a positive pressure applied to the fluid (blood, in that case) such that a leak in the tested circuit 110 would result in a loss of blood.

According to the invention, the drive/negative pressure device 100 generates a negative pressure on some intermittent schedule such that, at most times, fluid flows from the source 120 to the patient 115. At certain intervals, which may be triggered by the passage of a predetermined time or by detection of an event such as the displacement of a predetermined volume of fluid, the negative pressure is temporarily generated in the tested circuit 110. When this occurs, the negative pressure will draw air through any leaks in the tested circuit 110, which will appear as detectable air bubbles, triggering the air sensor 105.

Figure 2:
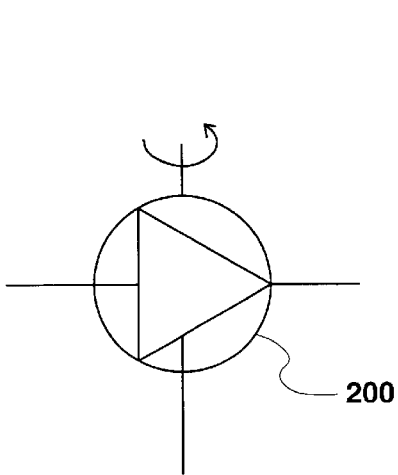
FIG. 2 is an example of an optional type of a drive/negative pressure-inducing device that may be used in the system of FIG. 1, in which flow is reversed by reversing a pump.

Referring to FIG. 2, one possible embodiment of the drive/negative pressure device 100 is simply a reversible pump 200. The pump 200 could be, for example, a peristaltic pump whose direction of rotation can be reversed. It could be any type of pump that can be reconfigured, such as by rotating a drive in a reverse direction, to reverse flow. The flow-reversal effect of this embodiment produces a negative pressure in the tested circuit 110 thereby drawing air into it and permitting detection of loss of integrity by the air sensor 105.

Figure 3:
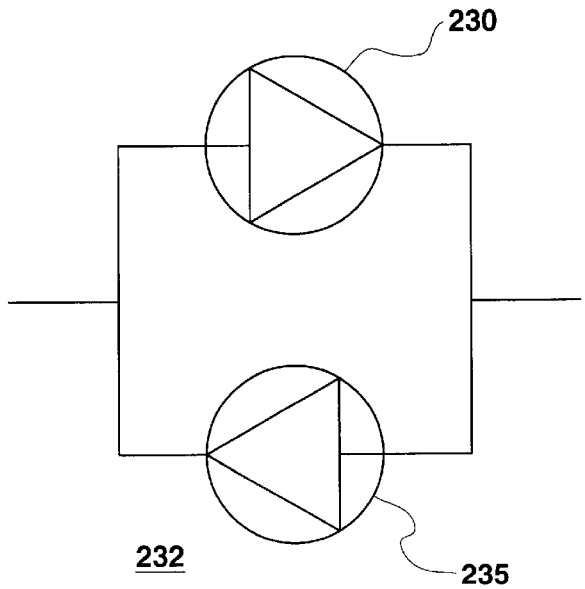
FIG. 3 is an example of another optional type of a drive/negative pressure-inducing device that may be used in the system of FIG. 1, in which flow is reversed by alternately actuating separate forward and reverse pumps connected in parallel.
Figure 4:
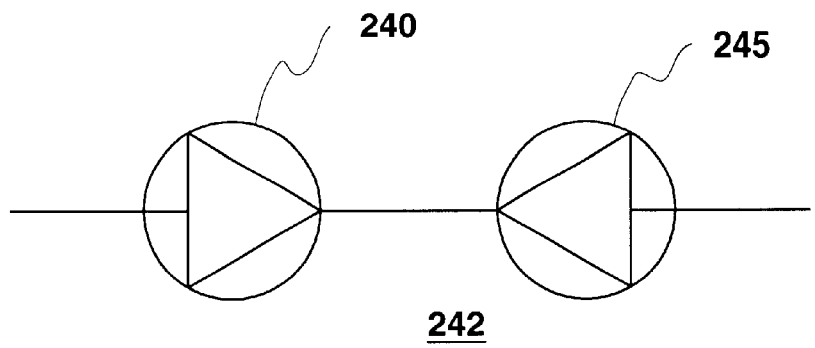
FIG. 4 is an example of still another optional type of a drive/negative pressure-inducing device that may be used in the system of FIG. 1, in which flow is reversed by alternately actuating separate forward and reverse pumps connected in series.

Referring now to FIGS. 3 and 4, another possible embodiment of the drive/negative pressure device 100 is a pair of pumps 230, 235 and 240, 245. In a parallel configuration 232, only one pump 230, 235 is actuated at a time, while the other 230, 235 blocks flow while it is idle to prevent short-circuiting. In a series configuration 242, only one pump 240, 245 is active at a time while the idle pump 240, 245 permits blood to flow through it. The flow reversal caused by both embodiments has the same effect as the embodiment of FIG. 2.

Figure 5:
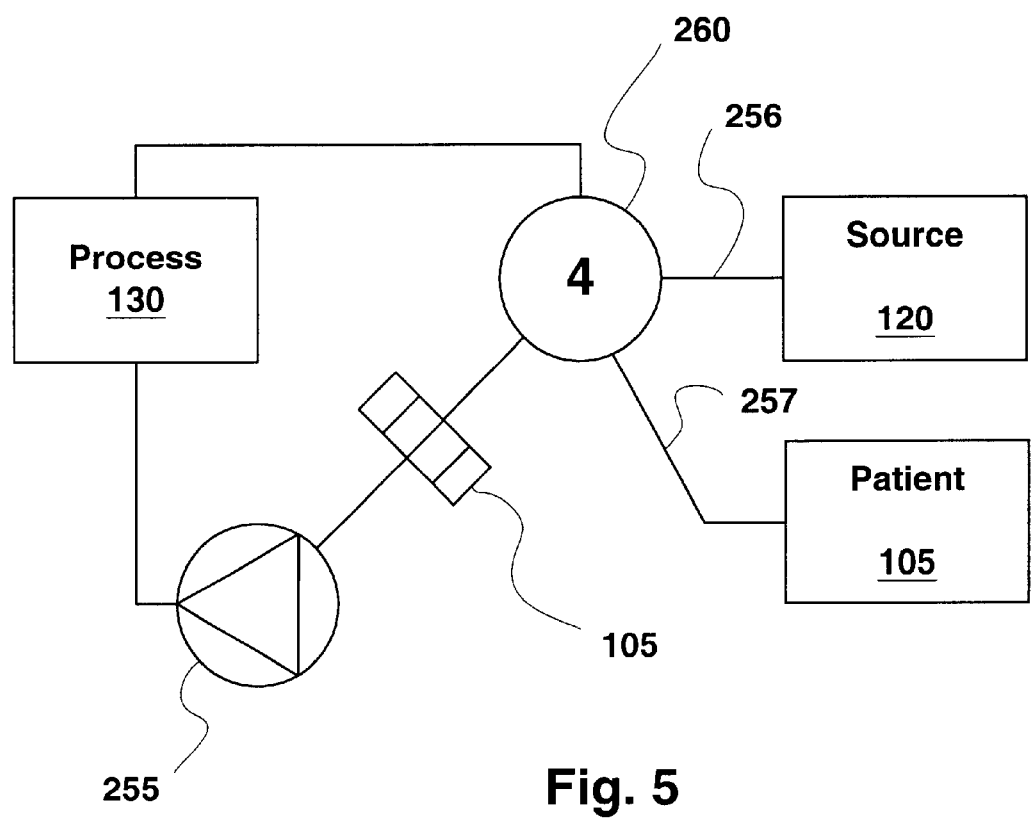
FIG. 5 illustrates yet another optional type of a drive/negative pressure-inducing device that may be used in the system of FIG. 1, in which flow is reversed by alternately switching a four-way valve.

Referring now to FIG. 5, still another possible embodiment of the drive/negative pressure device 100 employs a single pump 255 that pumps in a single direction. A four-way valve 260 transposes the input 256 and output 257 between the source of fluid 120 and the patient 115 such that a flow reversal results, as in the embodiments of FIGS. 2–4. A treatment process 130 is arranged in series with the pump 255.

Figure 6A:
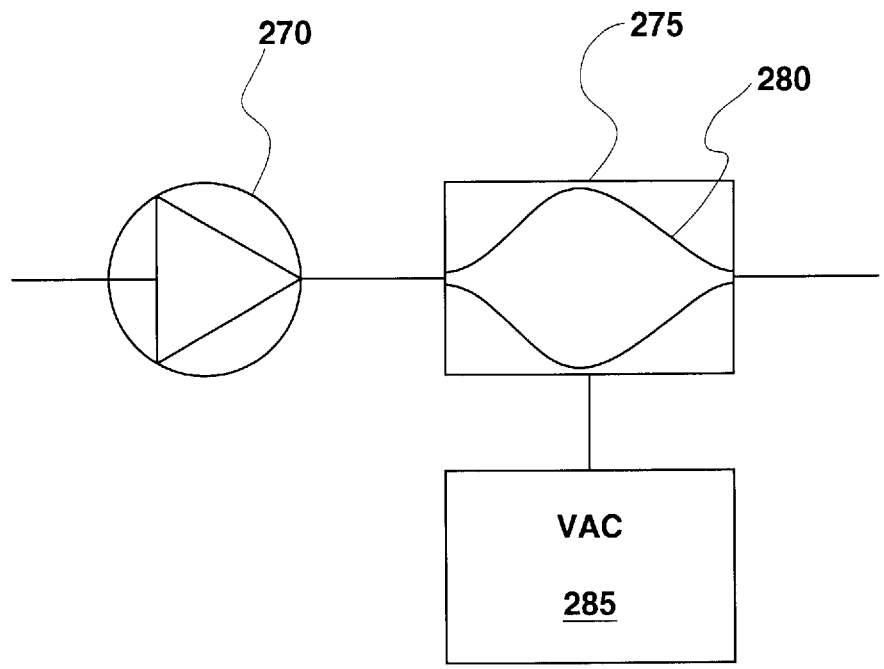
FIG. 6A is an example of yet another optional type of a drive/negative pressure-inducing device that may be used in the system of FIG. 1, in which flow is reversed by paroxysmal expansion of a bladder in the return circuit.
Figure 6B:
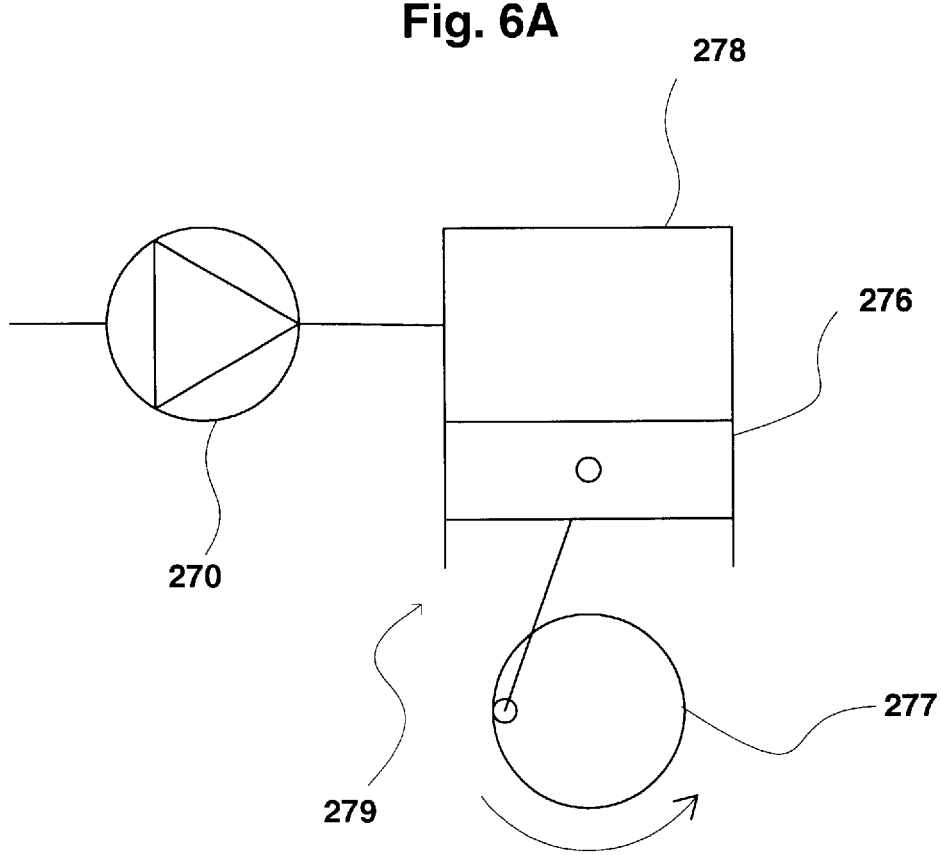
FIG. 6B illustrates an alternative device for creating a drive/negative pressure that may also be used in the system of FIG. 1, in which a negative pressure is generated by a syringe-type device.

Referring now to FIG. 6A, still another possible embodiment of the drive/negative pressure device 100 employs a single pump 270 that pumps in a single direction. Downstream of the pump 270, a bladder 280 forms part of the continuous exiting blood circuit. The bladder 280 may be expanded by a vacuum applied to a rigid casing 275, for example by a suction device such as a vacuum pump 285. Of course, the vacuum pump 285 may incorporate ballast because of the less-than-unity duty cycle of the negative pressure inducement cycle. Rapid expansion of the bladder 280 causes a negative pressure in the tested circuit with an effect that is generally similar to that of the foregoing embodiments. During the expansion of the bladder 280, the pump 270 may or may not be deactivated. Referring now to FIG. 6B, an alternative device for creating a negative pressure is a syringe 279 with a cylinder 278 and piston 276 driven by an automatic actuator 277. Note that, depending on the configuration of other components of the system to which the bladder 280 or syringe 279 (or equivalent device) is connected, it may be necessary to include a valve (not shown) to prevent backflow.

Figure 7A:
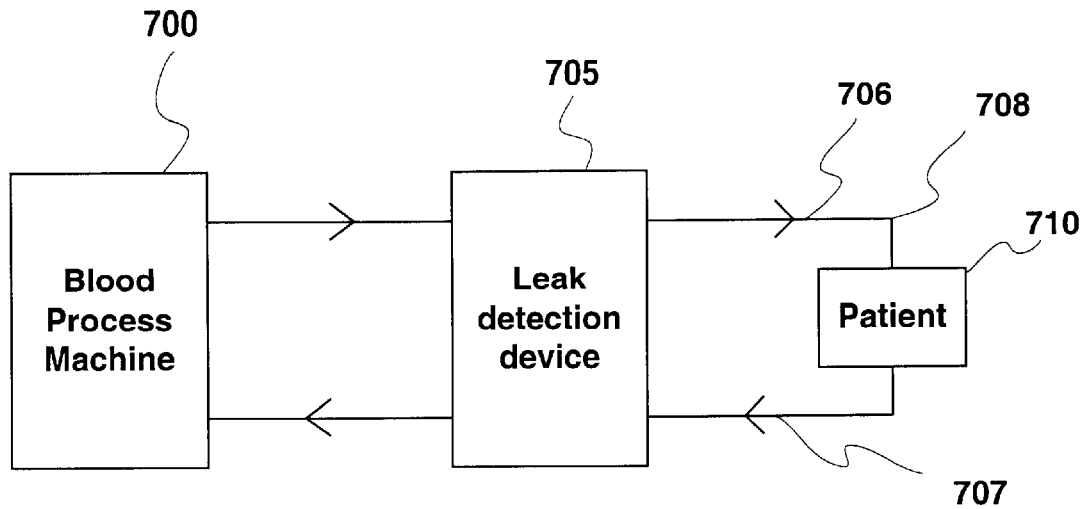
FIG. 7A is generalized diagram of a blood treatment device with a leak detector device add-on for treating the blood of a patient according to an embodiment of the invention.

Referring now to FIG. 7A, a blood processing machine 700 processes blood supplied to it from a patient 710 via a leak detection device 705. The blood processing machine 700 may be any type of device including hemodialysis, hemofiltration, hemodiafiltration, blood and blood component collection, plasmaphresis, aphresis, and blood oxygenation. The leak detection device 705 is configured such that blood flows as indicated by the arrows 706 and 707. The leak detection device 705, however, repeatedly generates a negative pressure in a return side 708 of the blood circuit thereby drawing air into that part of the circuit. This air can then be detected in various ways according to the way the blood processing machine 700 and/or leak detector device 705 are constructed. As should be clear, the leak detection device 705 can be added to any type of conventional or as yet unknown type of blood processing machine to provide return side leak detection.

Figure 7B:
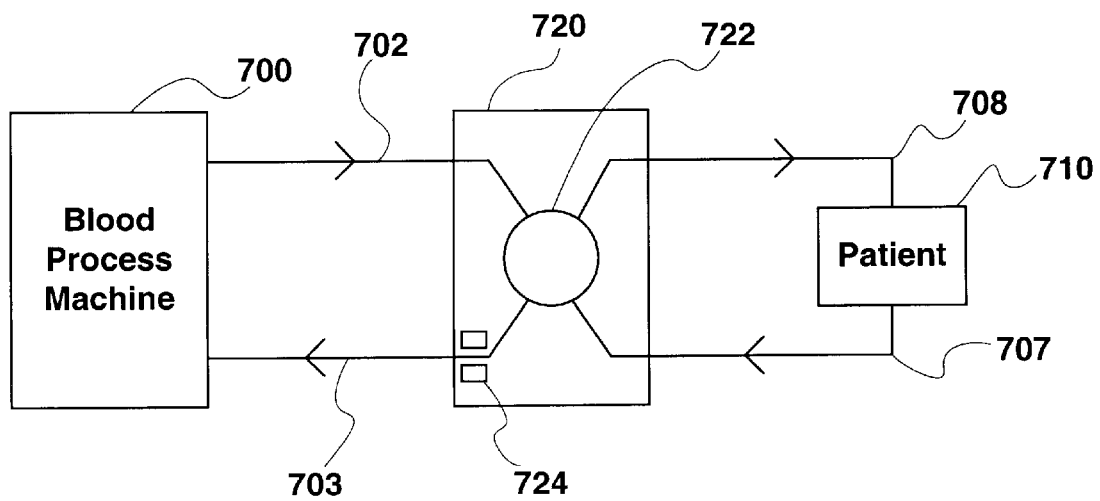
FIG. 7B is an illustration of an embodiment falling within the scope of the generalized embodiment of FIG. 7A in which a four-way valve is used to generate a negative pressure for leak detection.

Referring to FIG. 7B, one embodiment of the leak detection device 705 is shown at 720. The latter includes a circuit with a four-way valve 722 and an air sensor 724. A circuit is formed joining draw 707 and return 708 lines from the patient with the corresponding lines 702 and 703 of the blood processing machine through the four-way valve 722. The four-way valve 722 reverses the blood flow on the patient-side of the circuit without affecting the direction of blood flow through the blood processing machine 700. An air sensor 724 detects air in either the draw line 707 during forward operation and in the return line 708 during reverse operation. If air is detected, an alarm may be actuated or the circuit may be clamped to halt blood flow, thereby triggering a malfunction response in the blood processing machine 700 as illustrated in detail in the particular embodiment of FIG. 7E. Note that the air sensor 724 is not essential for practicing the invention if an air sensor is located in the blood processing machine 700. In that case, control of the leak detection device 720 would have to insure that enough fluid is displaced to permit detection by the air sensor in the blood processing machine 700.

Figure 7C:
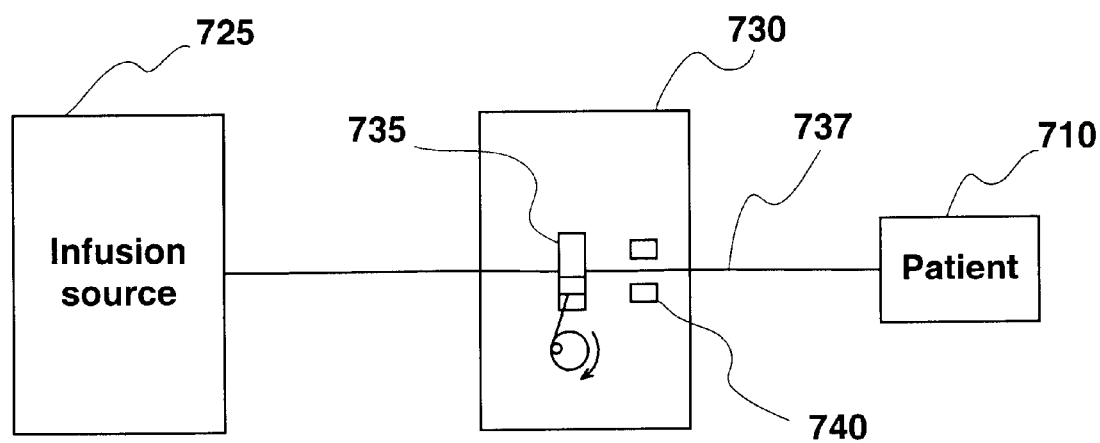
FIG. 7C is an illustration of an embodiment falling within the scope of the generalized embodiment of FIG. 7A in which a syringe device is used to generate a negative pressure for leak detection.

Referring now to FIG. 7C, a leak detection device 730, which can be added to an infusion pump 725, includes an automatic syringe or reverse pump 735 and an air sensor 740. A controller (not shown) causes the syringe or reverse pump 735 to reverse the flow through a circuit 737 leading to the patient 710 automatically. When the reverse flow occurs, the air sensor 740 detects any air drawn into the circuit 737 caused by any leaks. The same air sensor 740 can detect any leaks upstream of it at times when the syringe, or reverse pump 735, is not actuated. Note that the syringe or reverse pump 735 may be replaced by any suitable device such as that of FIG. 6A or 6B, a diaphragm pump, or any other suitable mechanism for creating a negative flow in a tested circuit.

Figure 7D:
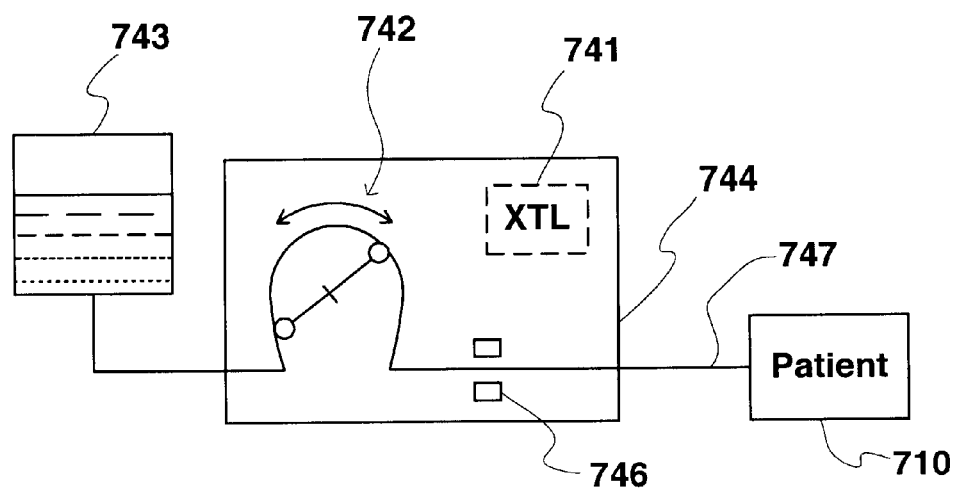
FIG. 7D is an illustration of an infusion device in which a reversible pump is used to generate a negative pressure for leak detection.

Note also that the infusion pump 725 itself may provide a mechanism for line testing if the pump within is made reversible as illustrated the embodiment of FIG. 7D. Referring now to FIG. 7D, an infusion pump 744 draws fluid from a reservoir 743 via a pump 742. An air sensor 746 detects any bubbles in the fluid stream. A controller 741 periodically reverses direction drawing air into the circuit 747, which can be detected during the reverse operation and responded to by an alarm, shutdown, or other appropriate action.

Figure 7E:
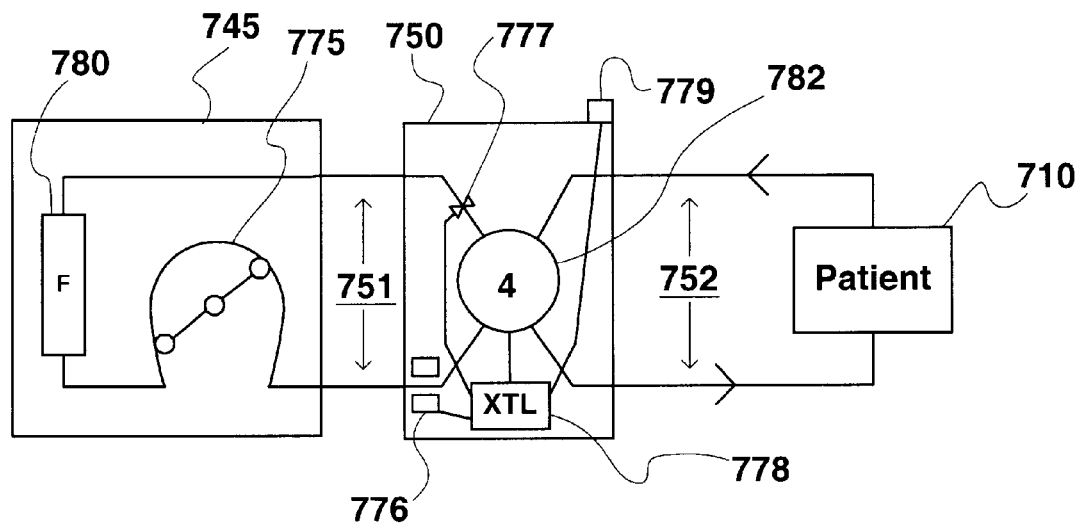
FIG. 7E is an embodiment falling within the scope of the generalized embodiment of FIG. 7A in which a four-way valve is used to generate a negative pressure and showing particular ways of responding to the detection of a leak.

Referring now to FIG. 7E, in another embodiment, a blood processing machine 745 and leak detection device 750 are interconnected as discussed with reference to FIG. 7A. Here the blood processing machine 745 contains a pump 775 and a filter or dialyzer 780. The leak detection device contains a four-way valve 782, which transposably interconnects the draw and return lines 751 of the blood processing machine 745 and the draw and return lines 752 of the patient 710 access. A controller 778 periodically and automatically switches the four-way valve 782, thereby causing air to enter any leaks in a return line and to be detected by an air sensor 776. The controller monitors the air sensor and may respond by actuating a clamp 777 and/or triggering an alarm 779. Actuating the clamp 777 can be used to trigger a malfunction response by the blood processing machine 745, which may have, for example, a pressure switch that would be activated by a clamped line.

Figure 7F:
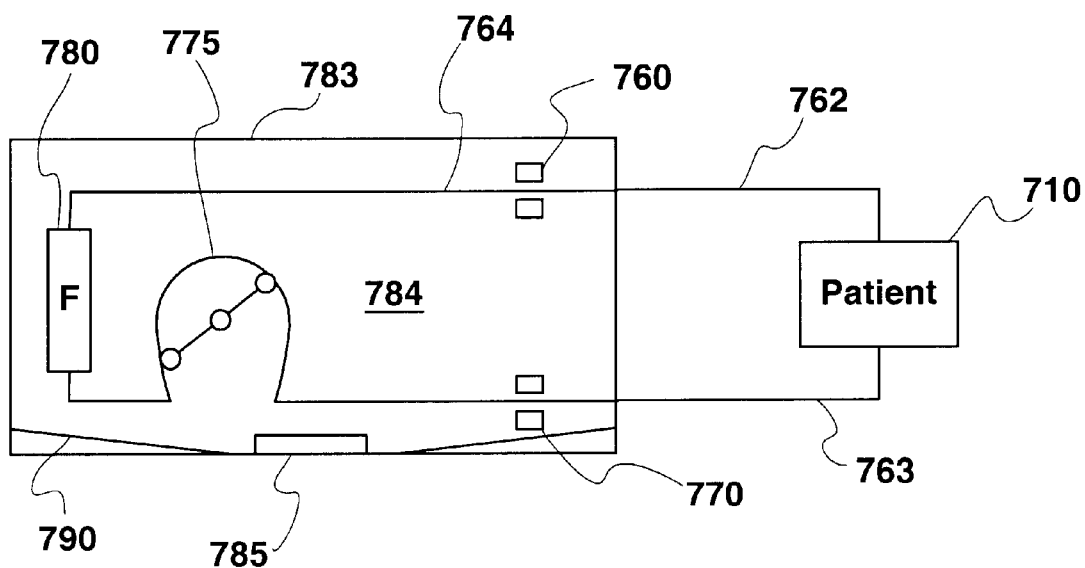
FIG. 7F is an embodiment of a blood treatment device with devices for leak detection according to an embodiment of the invention.

Referring now to FIG. 7F, leak detection features are built combined with those of a blood processing machine to form an integrated leak detecting blood processing machine 783. The latter contains air sensors 760 and 770, a filter 780, and a reversible pump 775, the latter being one mechanism for reversing flow to test the return circuit as discussed above in connection with other embodiments. Here, two air sensors 760 and 770, as should be clear from the discussion above, may quickly detect any leaks in draw and return accesses 762 and 763 when the pump is driven in forward and reverse directions, respectively. The embodiment of FIG. 7F also contains an additional leak detection feature by defining a funnel 790 at the bottom of an enclosure housing a housed portion 784 of a blood circuit 764 with a fluid detector 785 at the bottom of the funnel 790. Any leaks occurring in the housed portion 784 will be directed by the funnel 790 toward the fluid detector 785. The fluid detector 785 may be any suitable device for detecting blood, for example, a continuity tester. The fluid detector 785 may be linked to the same alarm system as the air sensors 760 and 770 and be responded to in the same manner as discussed in connection with any of the embodiments described herein.

Figure 7G:
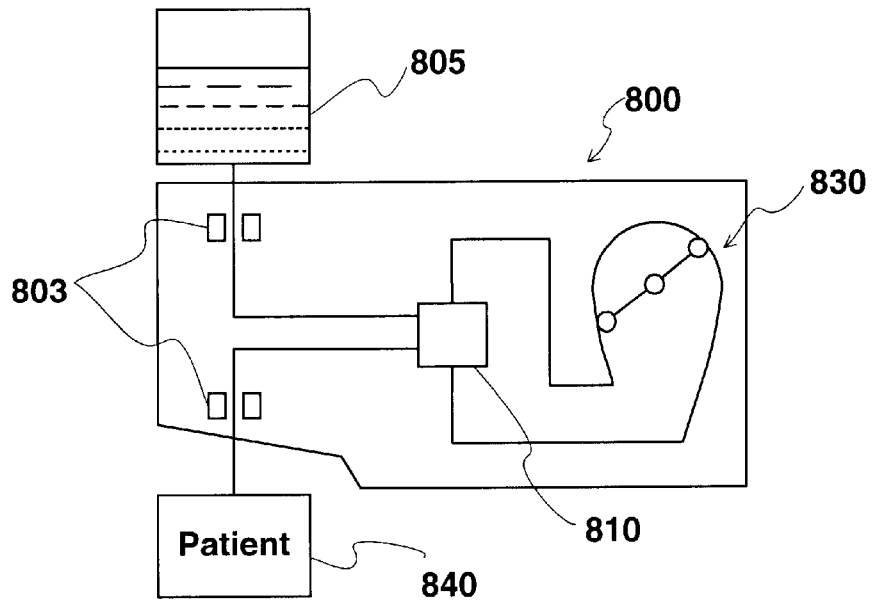
FIG. 7G is an infusion pump, with leak detection, employing a four-way valve to generate a negative pressure according to an embodiment of the invention.

Referring now to FIG. 7G a reservoir 805 of fluid to be infused is pumped through an infusion pump 800. The infusion pump has a pump 830, a four-way valve 810, and one or more air sensors 803. Normally, the four-way valve 810 is set to infuse fluid from the reservoir 805 to the patient 840. The four-way valve 810 is controlled to reverse periodically to check for leaks. The four-way valve 810 is connected such that fluid (which may include blood) flows back toward the one or more air sensors 803 indicating a leak.

Note that in the embodiment of FIG. 7G, the flow does not have to be reversed until the air reaches the air sensor 803. It need only be reversed until infiltrating air is transported to the four-way valve 810. This is because on the pump side of the four-way valve 810, the blood always flows in the same direction, so that the leak would be detected after forward operation carried the infiltrated air from the four-way valve to the air sensor 803. The same holds true for other embodiments, such as that of FIGS. 5, 7B, and 7E as well as other embodiments that employ four-way valves, such as those in FIGS. 8A and 8B.

Figure 8A:
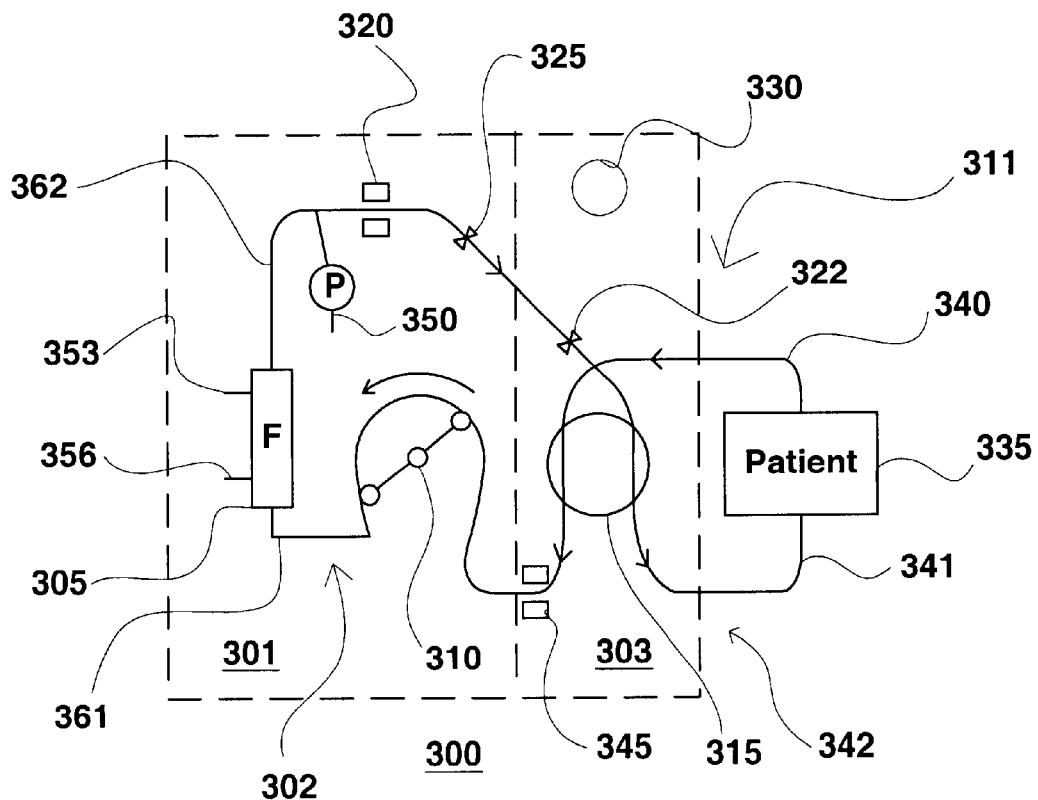
FIGS. 8A and 8B are more detailed diagrams of a two-access embodiment of a return circuit leak detector formed as a separate device from the hemofiltration or dialysis machine, shown in forward (FIG. 8A) and reverse (FIG. 8B) flow configurations, respectively, according to a preferred embodiment of the invention.

Referring now to FIG. 8A, an example of a two-access blood processing system 300 (illustrated as one for performing a hemofiltration or dialysis) combines a conventional blood processing machine (shown as a hemofiltration or dialysis machine) 301 with a venous disconnect sensor device 303. In this embodiment, the blood processing machine 301 may be of standard design with a separate venous disconnect sensor device 303 connected to it to provide the functionality of the embodiment of FIG. 1. Note that the separate venous disconnect device 303 allows retrofit of conventional blood processing machine 301 to provide the safety benefits of the invention. The blood processing machine 301 contains a dialyzer or hemofilter 305, which filters the blood passing through it. The dialyzer or hemofilter 305 contains connections 355 and 356 to a waste fluid or dialysate circuit and arterial 361 and venous 362 connections of a treatment circuit 302. A pump 310, which is illustrated by a peristaltic pump, pumps blood through the dialyzer or hemofilter 305, draws blood from the patient 335, and returns blood to the patient 335. Blood passes through the dialyzer or hemofilter 305 in one direction through a four-way valve 315 and then into a venous access 341 into the patient 335. Blood is drawn from an arterial access 340, passes through the four-way valve 315, and is supplied to the pump 310.

The blood processing machine 301 includes a venous return air sensor 320 located near the outlet of the dialyzer or hemofilter 305 in the treatment circuit 302. The latter detects any air in the blood prior to the blood being returned to the patient. The venous return air sensor 320 is standard on blood processing machines such as the hemofiltration and dialysis machine 301 and may be any type of air detector. For example, it may be an ultrasonic bubble detector as commonly used for detecting leaks in blood processing equipment.

A venous line clamp 325 selectively cuts off flow downstream of the venous return air sensor 320 as standard on blood processing equipment. The draw line air sensor 345 detects air in the arterial line downstream of the four-way valve 315 and upstream of the pump 310.

Figure 8B:
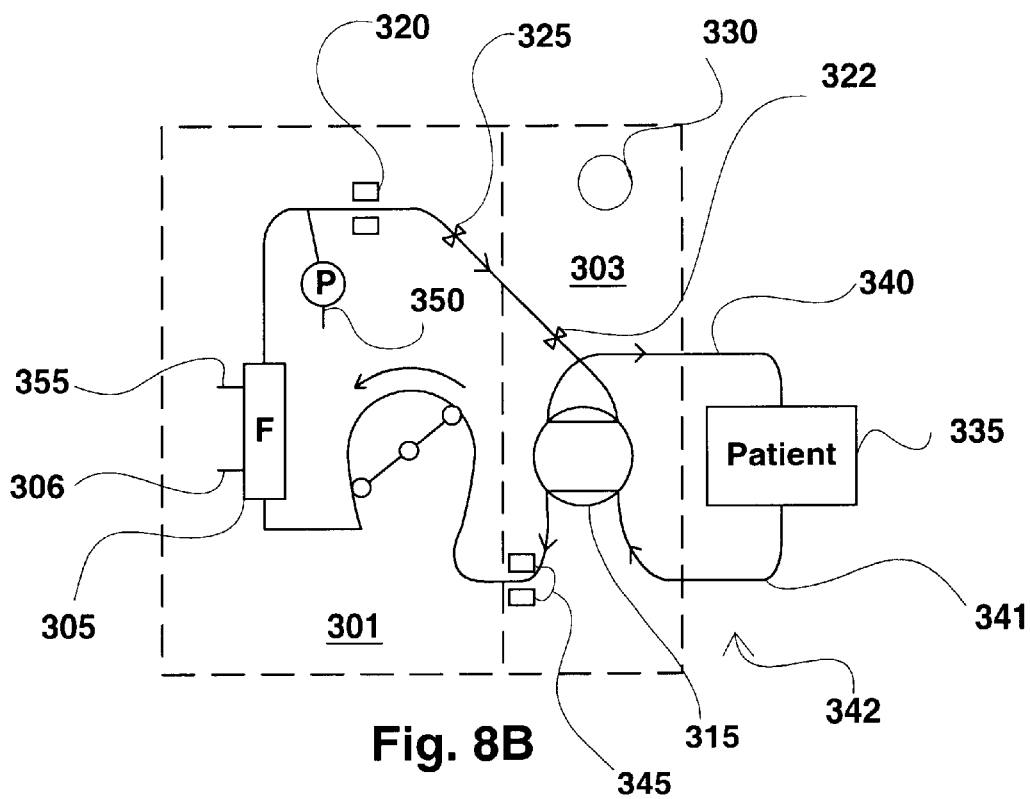

Referring now to FIG. 8B, periodically, the four-way valve 315 is switched to a reverse-flow position to cause blood to be drawn through venous access 341 and returned through the arterial access 340. The configuration of FIGS. 8A and 8B is instated only temporarily to cause air to infiltrate the venous circuit 342 through any leaks or disconnections in the venous circuit 342. The air infiltration may then be detected by the air sensor 345. Alternatively, the disclosed embodiment need not have the air sensor 345, but could rely for testing the venous circuit 342 on the air sensor 320 if the blood processing machine 301 has one. The only requirement would be that the flow be reversed long enough to displace any air bubbles from the leak to a point beyond the four-way valve 315 so that the pump will convey the air bubbles to the air sensor 320.

In the event air is detected by the air sensor 345 (or 320), the line clamp 322 is actuated shutting down flow through it and triggering a safety shutdown in the blood processing machine 301. Generally blood processing machines have such a safety mechanism that when flow through the blood processing machine 301 is halted, because of a fault like a crushed line for example, a venous pressure monitor 350 is triggered due to a resulting rise in venous pressure. This causes the blood processing machine 301 to stop the pump 310, set off an alarm, and clamp venous line clamp 325. Optionally, the venous disconnect sensor device 303 is provided with an alarm 330, such as an audio and/or visual signal to alert an operator to the shutdown.

The venous disconnect sensor device 303 may be connected to and used with a variety of different blood processing machines. Alternatively, its functionality may be integrated in any such machine. Also note that although the alarm event was described in the above embodiments as being triggered by a venous pressure monitor in the blood processing machine 301, it could be configured such that the air sensor 345 triggers an alarm directly.

It is conventional to make blood circuits disposable for reliability, ease of setup, and sterility. Thus, the entire tested blood circuit 110 of FIG. 1 and an entire blood circuit 311 (FIG. 8A) of the two-access hemofiltration system 300 may form a disposable unit. As a consequence, it may be desirable for the components to be as inexpensive as possible. Another desirable attribute of the components of a blood circuit is that it be hydraulically continuous, that is, that it provide no dead spaces that could cause stagnation of some of the blood flow. Another sometimes-beneficial feature of the components is that they be free from surfaces that rub together or have potentially stagnant capillary spaces such as seals. Together, these cost and hydraulic continuity requirements can impose significant constraints on the design of the four-way valve 315.

Figure 8C:
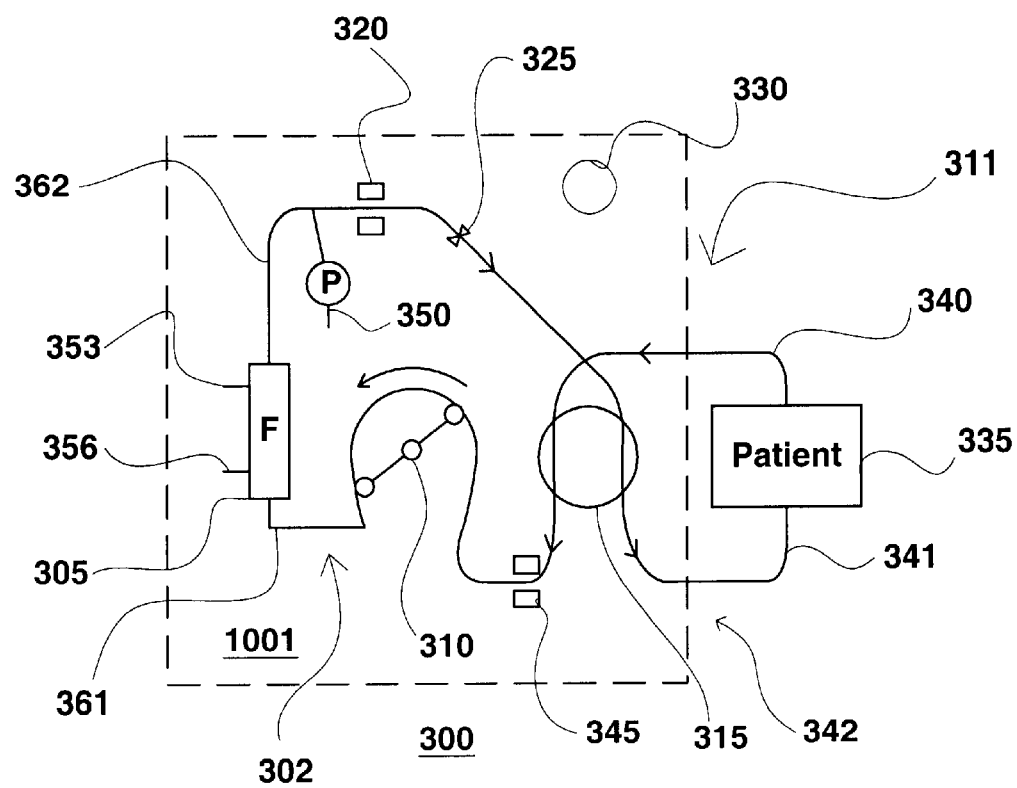
FIG. 8C illustrates a complete blood processing system with leak detection according to an embodiment of the invention.

Referring to FIG. 8C, a complete blood processing system with leak detection 1001 may conform to the details of the embodiment of FIGS. 8A and 8B. However, in that case, the line clamp 322 of FIGS. 8A and 8B may be omitted. Also, the air sensor 345 may be omitted, if desired, although it may provide an advantage of making it possible to detect leaks earlier. Components of FIG. 8C perform essentially the same functions as the identically-labeled components of FIGS. 8A and 8B and are therefore not discussed further.

Figure 9A:
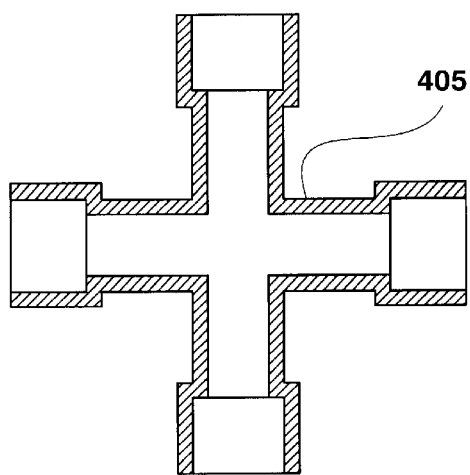
FIGS. 9A–9C illustrate a four-way valve that may be used to implement certain embodiments of the present invention.
Figure 9B:
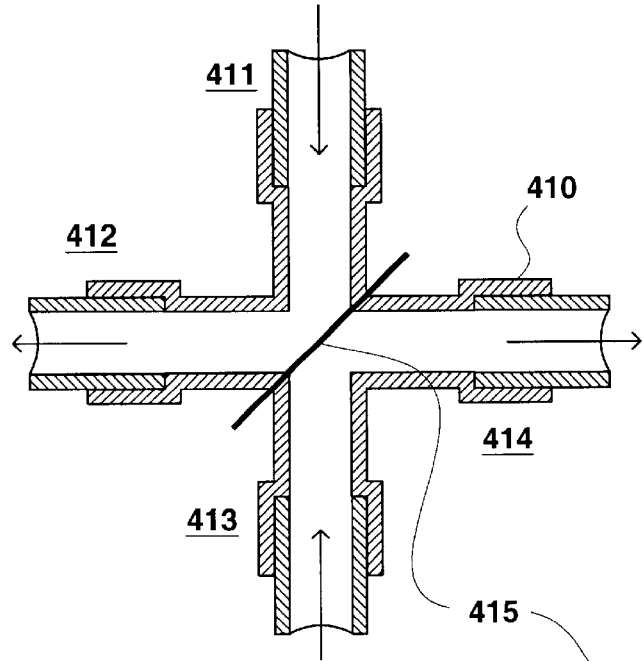
Figure 9C:
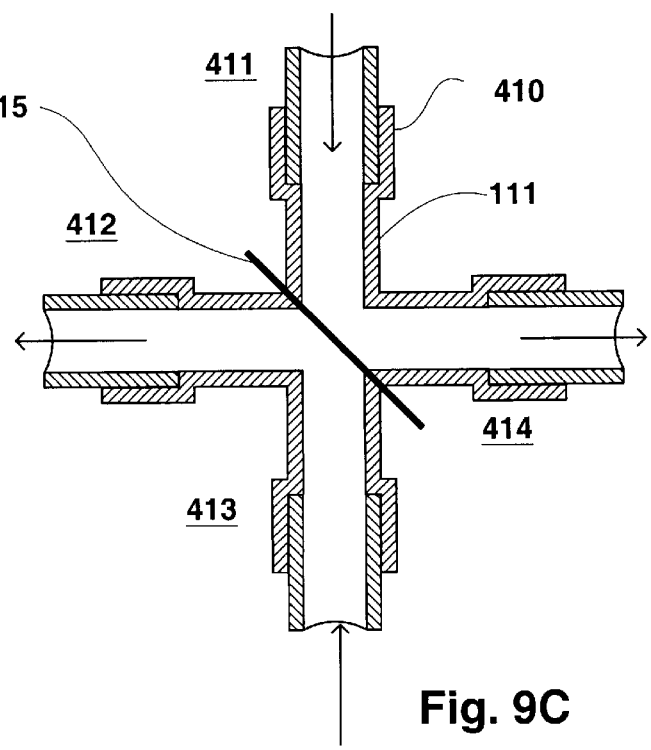

Referring now to FIGS. 9A–9C, a four-way valve body 405 is formed of a compliant injection moldable polymer. The valve body 405 has four ports 411, 412, 413, and 414. Each port has a flanged portion, for example as indicated at 410, permitting tubing to be inserted and bonded to the valve body 405. Each port 411, 412, 413, and 414, may be selectively joined to either of two adjacent ports by forcing an anvil-edge 415 against the center of the valve body 405 in one of two orthogonal directions as shown in FIGS. 9B and 9C. In FIG. 9B, the anvil-edge is pressed in a first direction joining ports 411 and 412 and simultaneously joining ports 413 and 414. In FIG. 9C, the anvil-edge is pressed in a second direction joining ports 411 and 414 and simultaneously joining ports 412 and 413. As can be seen by inspection, the flow passages form by pinching the valve body 405 are free of dead flow zones in both configurations.

Figure 10A:
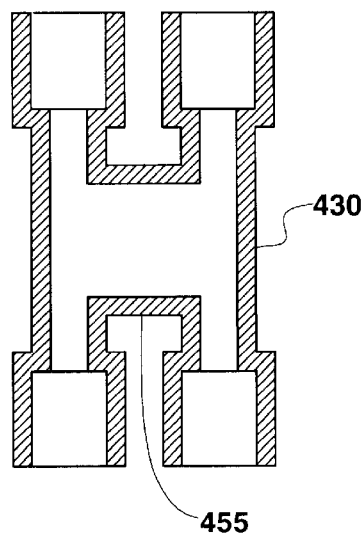
FIGS. 10A–10C illustrate another four-way valve that may be used to implement certain embodiments of the present invention.
Figure 10B:
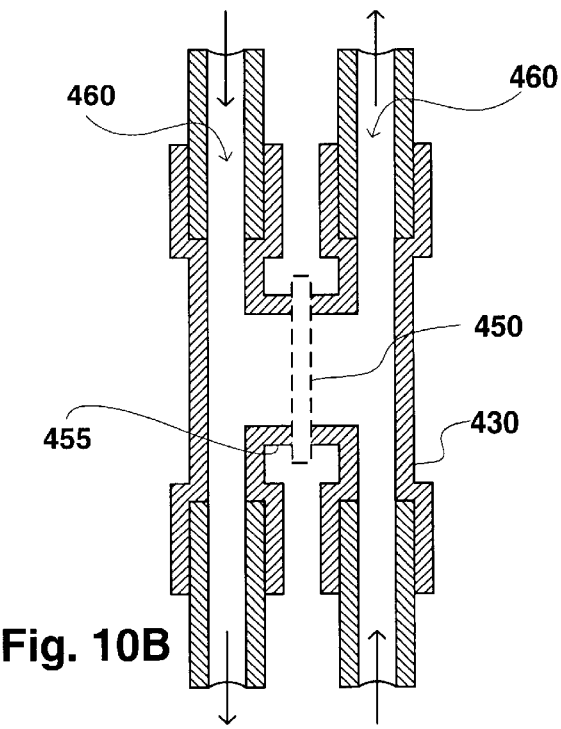
Figure 10C:
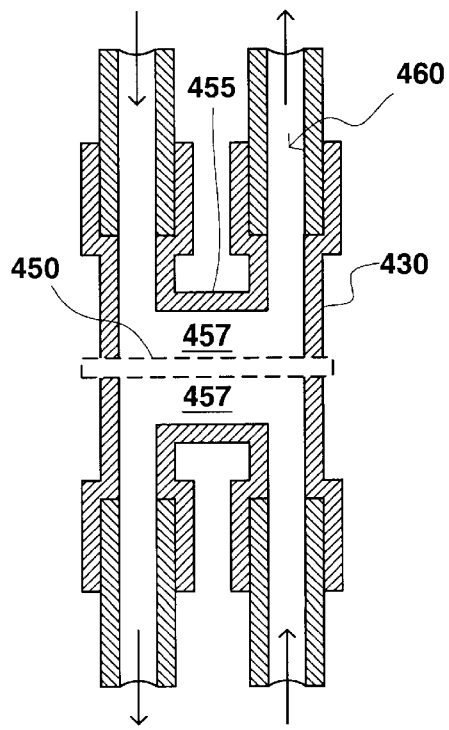

Referring now to FIGS. 10A–10C, in an alternative embodiment, a valve body 430 is formed in the shape of an "H." To form a first flow configuration (FIG. 10B), an anvil-edge is perpendicular to the first orientation and pinches the bridge to bisect it and form two parallel channels 460. To form the second flow configuration (FIG. 10C), the anvil-edge 450 pinches the H-shaped bridge 455 longitudinally along the centerline of the crossing line 455 of the "H" to form mirror image U-shaped channels 457.

In the above four-way valve embodiments, the anvil edges 415, 450 may be actuated by solenoids. Referring now to FIGS. 11A–11D, one way to activate both orientations of the anvil edge 405/415, 450 with a single solenoid is by disposing two perpendicular anvils 510 and 515 on opposite sides of the valve body 540. One anvil 515 may be urged toward the valve body 540 by a spring 550 while the other is forced by the solenoid 560. When the solenoid 560 is retracted, only the spring-urged anvil 515 deforms the valve body 540. When the solenoid 560 is extended, only the solenoid-forced anvil 510 deforms the valve body 540. Here, FIG. 11A shows the spring urged anvil 515 is pressed along the bridge (parallel to the length of the bridge of the "H") as viewed from the side and FIG. 11B shows the same configuration as viewed from the top. FIG. 11C shows the solenoid urged anvil 510 pressed across and bisecting the bridge of the "H" as viewed from the side and FIG. 11D shows the same configuration as viewed from the top. Support tables 520 and 525 provide support for parts of the valve body 540 that are not otherwise supported by the anvils 510 and 515.

Figure 12A:
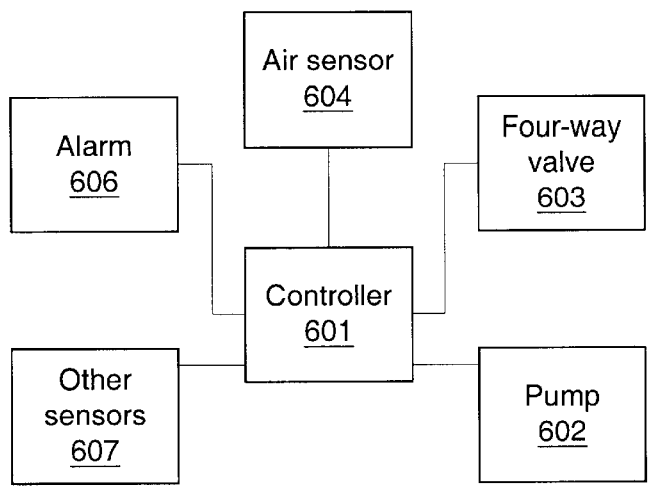
FIG. 12A is an illustration of functional components of a control system that may be used to control certain embodiments of the invention.

Note that the functionality of FIG. 1 may be provided in a fully integrated system rather than as an add-on to a conventional blood processing machine 301 as illustrated in the embodiment of FIGS. 8A and 8B. That is, the components of the venous disconnect sensor device 304 may be integrated in the blood processing machine 301 as is readily apparent from the figure. Note also that the air sensors 320 and 345 may be combined with other sensing mechanisms in a fuzzy logic circuit or network classifier to enhance the robustness and sensitivity of leak detection. Thus, the inventive technique may be combined, for example, with fluid sensing as described in PCT application US98/19266, combined with venous pressure monitoring as outlined in International Standard IEC 60601-2-16. These inputs may then be combined to reduce false positives and enhance sensitivity through fuzzy logic or state-classification techniques. Referring now to FIG. 12A, a control mechanism for an embodiment of the invention includes a controller 601, which could be a programmable microprocessor, mechanical, or electromechanical controller. The controller 601 is connected to receive inputs from an air sensor 604 and, optionally, other sensors 607. The controller 601 is also connected to control an alarm output 606, a pump 602, and a four-way valve 603. Generally, and consistent with other embodiments, the controller 601 may control other types of drive/negative pressure devices 100 as should be clear from the present disclosure. The other sensors 607 may include any (or none) of the fluid detectors and pressure sensors or any other sensors including those of the prior art. In the controller embodiment of FIG. 12A, any, or all, of the sensor inputs may be used in combination or alone to trigger an alarm state, preferably one accompanied by shutdown of the pump 602.

Figure 12B:
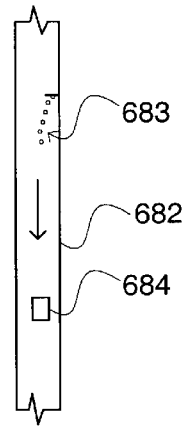
FIG. 12B is an illustration of the use of a sound sensor to sense air infiltration without requiring the direct sensing of a presence of air, such as is required by an ultrasonic air sensor.

Referring to FIG. 12B, note that the air sensor 604 may be any kind of sensor capable of detecting either the intrusion of air into a circuit or the presence of air in the circuit. Air infiltrating a line may create sound for example, as bubbles 683 are generated by the infiltration. Such a sound may be detected with, for example, an audio sensor such as a hydrophone 684. A signal from a hydrophone 684 could be classified by an audio pattern recognition engine programmed into the controller 601 to screen out other sounds. In such a case, in the embodiments discussed above, air does not need to be drawn all the way to the air sensor 604 for infiltration to be detected; rather the audio signals may travel through the lines 682 in the fluid media to the sensor 684. Note that a hydrophone may be detect sounds without being immersed in the fluid itself, as long as appropriate acoustic measures are taken to minimize attenuation through any barriers. Other types of disturbances or machine-recognizable features may form a basis for detecting air infiltration such as optical, vibrational, chemical, etc.

Note that the controller 601 need not be the ultimate originator of command signals for the reversing (or negative pressure) cycles. So, for example, a signal for triggering the reversing (negative pressure) cycles could originate from a different source, for example a conventional blood processing system and be converted into a control signal by a final control (e.g. 601) to govern the reversing (negative pressure) cycle. Such an embodiment would be well within the scope of the invention as claimed below.

The controller 601 may also be responsible for controlling the timing of the periodic flow reversals. To this end, the pump 602 may be configured to output encoder pulses to the controller 601 to allow the controller 601 to cumulate the volume of blood displaced in a given direction.

Referring now again to FIGS. 8A and 8B in addition to FIG. 12A, in normal operation, the system of FIGS. 8A and 8B pumps blood from the arterial access 340 processes it, and returns treated blood to the patient through a venous access 341. With the peristaltic pump, 310, it is possible by counting the number of rotations of the pump to determine accurately the volume of blood displaced. To insure a high level of insurance against blood loss, a maximum tolerable blood loss may be determined and used to control the periodic negative pressure cycles, for example in the hemofiltration system 300. Note that in determining maximum limits, due consideration must be given to the fact that some of the patient's blood is already outside of his/her body in the circuit of the machine. If the maximum volume of blood displaced between negative pressure cycles is no greater than the maximum tolerable blood loss, then even a full disconnect of a lumen could never result in more than the maximum tolerable blood loss. Thus, the period of the flow reversal cycles can be set to a value that is no greater than a ratio of the maximum allowable blood volume loss to the volume flow rate of the blood. Thus, if the maximum blood loss a patient can tolerate is 500 ml. and the rate of flow of blood is 500 ml./min., the period of the flow reversal cycles should be no greater than one minute. The period between cycles, as mentioned elsewhere, can be determined by calibrated timing, by direct measurement of mass or volume flow, or by other means effective to insure the amount of blood does not go beyond some safe limit.

The duration of each negative pressure cycle is best determined by how long it takes to draw the entire quantity of blood in the circuit between the terminal end of the patient's venous access and a point where it is inevitable that the infiltrated air will reach an air detector (e.g., 345). In a system with a four-way valve, this may be the point where the air is just beyond the four-way valve, where the blood runs through the circuit in the same direction irrespective of the position of the four-way valve. For example, in the embodiment of FIGS. 8A and 8B, so long as air reaches a point between the four-way valve 315 and the air sensor 345, the pump will insure that it gets to the air sensor 345 once it is on the treatment circuit 302 side of the four-way valve 315, which only runs in direction. Thus, the duration of the negative pressure cycle need only insure that a leak at the most remote end would cause air bubbles to be drawn all the way to an air sensor.

The above control protocols, although not required, are desirable. These protocols may be implemented by suitably calibrated timing of control signals, by counting pump revolutions, by direct measurement of blood flow volume, or any other suitable technique.

The maximum allowable blood loss, which may be used to determine the maximum time between leak test cycles, may be made a programmable value that can be entered in the controller 601. Each patient may be evaluated and a maximum threshold established specifically for him/her. Alternatively, the controller could be connected to an electronic scale, which generates a maximum tolerable blood loss value based on the patient's weight.

Note that although in the embodiments described above a peristaltic pump was disclosed, this is only an example and it is clear that a variety of different types of pumps may be used with the invention. For example, a diaphragm or turbine pump may also be used in place of any of the pumps disclosed. Note also that although a four-way valve, a reversible pump, an expanding bladder, and connected pairs of pumps were described as mechanisms for reversing flow, it is clear that other mechanisms can also be employed. Each of the examples of a pump and a valve or reversible pump, or pump combinations, amounts to a different reversible conveyance. Note also that it is possible to practice the invention, as indicated in the discussion of FIGS. 6A and 6B, without reversing flow in the entire blood circuit, but only within a portion by creating a short term negative pressure and negative local flow. Other mechanisms may be used for accomplishing this negative pressure and flow, such as a negative flow pump arranged in the blood return circuit and opposing the main pump with a take-up ballast vessel between them to permit the negative flow pump to run for a period in the reverse direction without reversing the flow in the entire circuit.

Note also that although in the above detailed illustrations, a hemofiltration or dialysis application of the invention was described, it is clear the invention is applicable to many different systems in which blood is circulated outside the body. For example, the system may be used to avoid waste of blood or insure the satisfaction of a critical need, during transfusion. Some other examples of applications are hemodialysis, hemofiltration, hemodiafiltration, blood and blood component collection, plasmaphresis, aphresis, and blood oxygenation.

Note also that although the invention was discussed in connection with embodiments in which blood is drawn from an arterial access and returned through a venous access, it is clear from the disclosure that the reverse could be the case. Also, neither the forward and reverse flow directions need be preferred. The duty cycle of the reverse (leak test) flow direction to that of the forward direction may be any ratio, including 50%.

Figure 13:
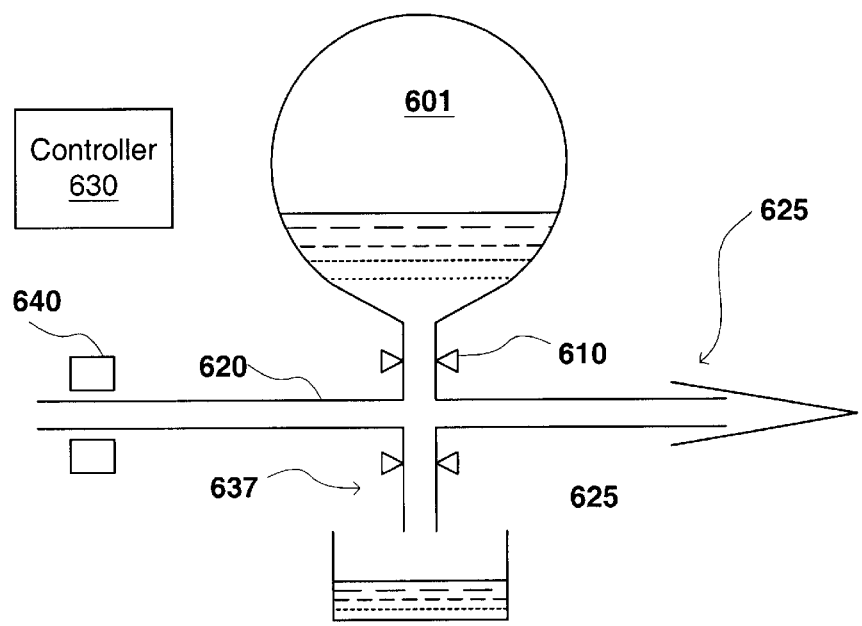
FIG. 13 is an illustration of a portion of a blood circuit in which some other fluid is added for testing purposes and either subsequently rejected or subsequently supplied to the patient.

Referring now to FIG. 13, a fluid other than blood may be drawn or injected for line-testing purposes rather than relying solely on blood drawn from the return line. This may be useful in instances where the venous access cannot supply a great deal of blood. For example, as shown in FIG. 13, sterile fluid from a reservoir 601 may be allowed to flow into a junction 605 through a cutoff valve 610 when the flow is reversed or a negative pressure generated. Any leaks would be detectable in the fluid, as they are detected, as discussed above. In this case, the only blood that need be drawn through a draw access 615 is the volume necessary to fill the circuit 620 between the remote terminus 625 of the access and the junction 605. A control system 630 may open the cutoff valve 610 permitting fluid from the reservoir 601 to enter the junction 605 only after at least a sufficient volume of blood had been drawn from the remote terminus 625 to fill the circuit between the remote terminus 625 and the junction 605. A volume of fluid, possibly along with blood, would then be drawn at least sufficient to fill the circuit between the point where it is inevitable that the air will arrive at an air sensor 640. In this case, the volume might be the volume of the circuit from the remote terminus 625 right up to (or sufficiently near) the air sensor 640 to be detected. When flow is again reversed, the fluid may be drained to a waste collection container 635 or returned to the patient. The former option may be implemented through a suitable flow diverter mechanism 637 such as used to let fluid in.

Figure 14:
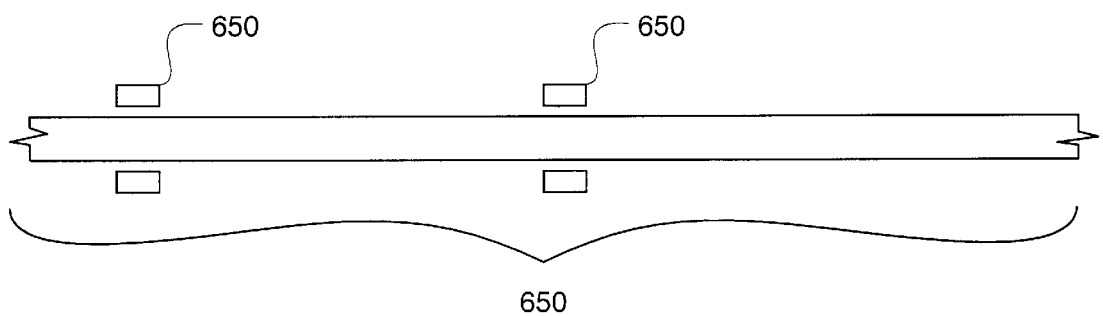
FIG. 14 is an illustration of how additional air sensors can be added to a blood circuit to reduce the quantity of blood that must be displaced for a test.

Note that in many of the above embodiments, a single air sensor is shown. It is clear that multiple air sensors may be used in a single line and spaced apart by an equal volume of displaced fluid/blood so that the volume of blood/fluid that must be pumped in reverse can be reduced. Thus, referring to FIG. 14, if a two air sensors 650 are used in a given circuit portion 655 rather than only one, the amount of fluid/blood that has to be displaced in the circuit in order to test it fully for leaks can be reduced substantially by half.

Figure 15:
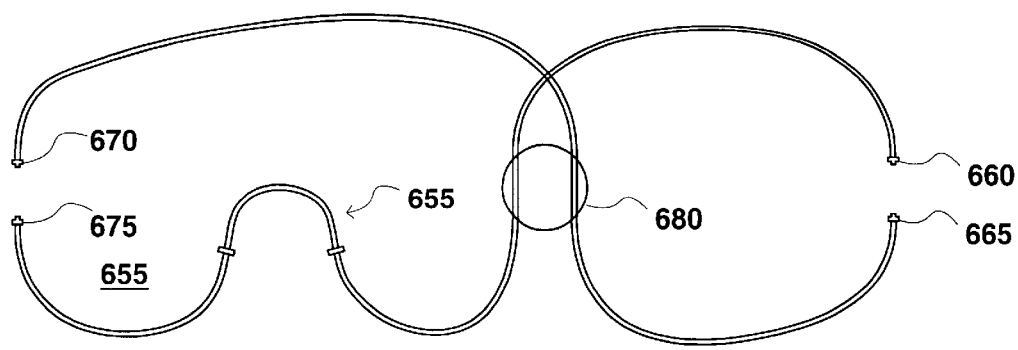
FIG. 15 is an illustration of a blood line for use with certain embodiments of the invention.

Referring now to FIG. 15, a blood line 655 has two access ends 660 and 665 adapted to be connected to a patient for draw and return of blood. Two filter ends 670 and 675 are connected by a valve portion 680 to the access ends 660 and 665 and adapted to be connected to a filter or other treatment device (not shown). Alternatively, the filter ends 670 and 675 may be connected to a filter (not shown) at the point of manufacture and sealed and sterilized with the entire blood line shown. The valve portion 680, preferably, is a blood contact portion of a complete flow diverting device that may be, for example, the valve body parts 405, 430, 540 of the four-way valves illustrated in FIGS. 9A–9C, 10A–10C, and 11A–11D, any of those examples in applications incorporated by reference above, or any of those of the prior art. The valve portion 680 switches the direction of the flow of blood between the access ends 660 and 665. The bloodline 655 also has a portion 656 adapted to be driven by a pump, such as a peristaltic pump (not shown).

The bloodline of FIG. 15 may be a replaceable device that is packaged with instructions 667 explaining how it may be used with a blood processing machine such as any of the embodiment discussed above. It may be configured to provide the fluid conveyance line for both the blood processing machine and leak detection device portions of any of the above embodiments, such as embodiments configured along the lines of FIG. 7A or complete systems like. The blood line 655 has only the basic elements, and in a practical implementation would be expected to include one or more of the following: injection sites, luer connectors, drip chambers, transducer protectors, manual line clamps, access lines, access needles, dialyzers, filters, protective caps, etc. Preferably the entire blood line is manufactured and then sterilized, for example, by gamma rays, steam, or other means.

Note that although in the embodiments described above the inventive leak detection method and device are applied to extracorporeal blood circuits, the invention has other applications as well. For example, circuits used for infusion of costly (or time-critical) drugs may be monitored using the invention.

Figure 16:
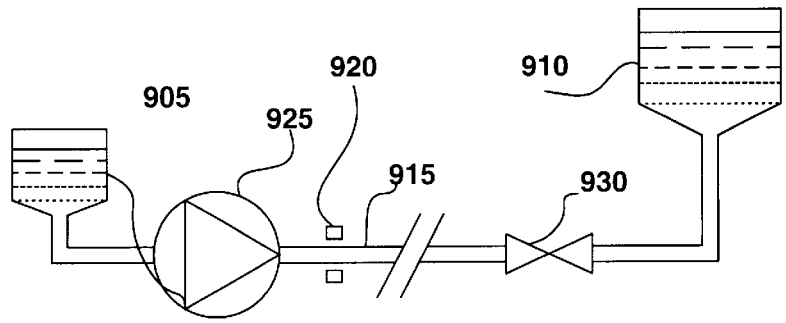
FIG. 16 is an illustration of an infusion system with leak detection according to an embodiment of the invention.

In fact, the invention may be applied to fluid conveyance systems that are unrelated to human or animal treatment. Referring now to FIG. 16, the invention is applicable to a wide range of liquid conveyance systems. FIG. 16 shows a generalized liquid conveyance system in which a liquid is conveyed from a source 905 to a sink 910. A pump 925 forces the liquid along a channel 915 whose integrity is to be tested. An air sensor 920 is located at some point along the line. A throttling device 930 may or may not be required. In one flow direction, the liquid is conveyed from source 905 to sink 910 under positive pressure in the channel 915. Automatically and repeatedly, a negative pressure is generated in the channel 915, for example by operating the pump 925 in reverse. The negative pressure draws air into the liquid in the line if there are any leaks in the line. The air is detected by the air detector 920 and the leak is revealed. Any liquid conveyance system may be tested in this way, as long as a negative pressure can be generated selectively using any of the techniques (or any others) as discussed above. Note also that the source and sink may be identical. For example, the system might circulate liquid through a processing system such as a heat exchanger or a reaction processor with a catalyst or other such processing system.

Note that although in the embodiments described above, leaks are betrayed by the detection of a presence of air into the tested line, other techniques are possible in other embodiments of the invention. For example, rather than detect a presence of air, it is possible to detect the infiltration of the air as it occurs. For example, an acoustic signal may be generated by bubbles as they are drawn into the tested circuit. This signal may be detected by an acoustic sensor. Also, air bubbles flowing through the line may be detected by other means such as an acoustic signal of bubbles passing by an acoustic sensor. Various velocimetry techniques are affected by air, for example vortex shedding velocimeter, orifice plates, and other such devices. The presence of air may be detected by optical means as well.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A leak detector comprising:
   at least one actuator controlled by a controller, said at least one actuator being configured to control pressure in a blood circuit, said controller configured to control flow in said blood circuit and detect a loss of integrity in said blood circuit, by:
      delivering blood to a patient through the blood circuit during first time including applying a positive gauge pressure to said circuit;
      applying a negative pressure to said blood circuit during second time;
      detecting a presence of air in said blood circuit during at least a portion of said second time or after said second times, such that air infiltrating said blood circuit during said second time as a result of said negative pressure and a presence of a leak is detected.

2. A detector as in claim 1, wherein said controller is further configured to wait passage of a predetermined volume of blood into said patient prior to applying said negative pressure.

3. A detector as in claim 1, wherein said controller is further configured such that said applying a negative pressure includes reversing a direction of flow of blood in said blood circuit.

4. A detector as in claim 1, wherein said controller is further configured such that said applying a negative pressure includes switching a valve to cause blood to flow in a reverse direction through said blood circuit.

5. A detector as in claim 1, wherein said controller is further configured such that said applying a negative pressure includes changing a volume of a portion of said blood circuit.

6. A detector as in claim 1, wherein said controller is further configured such that said detecting includes detecting air bubbles in blood.

7. A detector as in claim 1, wherein said controller is further configured such that:
   said applying includes reversing a direction of flow of blood in said blood circuit;
   said detecting includes detecting air with an air sensor located to detect air at a specified position in said blood circuit; and
   a duration of said second time is at least long enough to insure that blood will ultimately flow from a terminus of said blood circuit to said specified position, whereby leakage of blood in said blood circuit at least between said specified position and said terminus is assured.

8. A leak detector, comprising:
   a mechanism operative to reverse flow in a blood circuit configured to return blood to a patient such that a negative pressure is generated in said blood circuit;

an air sensor positioned with respect to said blood circuit to detect air drawn into said blood circuit in the event of a loss of integrity in said blood circuit;

a controller connected to control said mechanism such that said negative pressure is of sufficient magnitude and duration as to insure that blood at a remote end of said blood circuit connected to said patient is drawn to point where it is detectable by said air sensor.

9. A leak detector as in claim 8, wherein said mechanism includes a four-way valve.

10. A leak detector as in claim 8, wherein said mechanism includes a controller configured to reverse said flow iteratively after successive displacements of a predetermined volume of blood.

11. A leak detector as in claim 10, wherein said predetermined volume corresponds to no more than a maximum tolerable volume of blood that can be lost without injury to a patient.

12. A leak detector as in claim 8, wherein said mechanism connects said blood circuit with a therapeutic process to which blood circulated through said blood circuit is subjected.

13. A leak detector connectable to a blood processing machine that has an access blood circuit connectable to a patient to remove blood from, and deliver blood to, said patient; a process blood circuit including a treatment component for treating blood circulated through said process blood circuit, said leak detector comprising:

a reversible conveyance connected to move blood through said process and access blood circuits;

an air detector in said access circuit;

a controller configured to reverse said conveyance periodically to draw air into any leaks in said blood circuit and to control said conveyance such that said air is moved to said air detector, whereby a leak in said access blood circuit may be detected.

14. A detector as in claim 13, wherein said controller is configured to reverse said conveyance such that a volume of blood at least as great as a volume of said access blood circuit between said air detector and a remote terminus of said access blood circuit.

15. A detector as in claim 13, wherein said conveyance has a four-way valve and is configured to reverse by switching said four-way valve.

16. A detector as in claim 13, wherein said air detector detects air bubbles in fluid.

17. A detector as in claim 13, wherein said controller is configured such that said conveyance is reversed sufficiently frequently that no more than a minimum safe quantity of blood is lost due to a leak before said leak is detected.

18. A leak detector connectable to a device operative to control a flow of blood through a blood circuit, said leak detector including a controller programmed to implement a method of detecting a leak in a fluid circuit supplying fluid to a patient, comprising the steps of:

delivering fluid to a patient through a circuit during a first time;

applying a negative pressure to said blood circuit during a second time;

detecting a presence of air in said fluid circuit during at least a portion of said second time or after said second time such that air infiltrating said fluid circuit during said second time as a result of said negative pressure is detected.

19. A detector as in claim 18, wherein said method includes waiting for the passage of a predetermined volume of fluid into said patient prior to applying said negative pressure.

20. A detector as in claim 18, wherein said step of applying a negative pressure includes reversing a direction of flow of fluid in said fluid circuit.

21. A detector as in claim 18, wherein said step of applying a negative pressure includes switching a valve to cause fluid to flow in a reverse direction through said fluid circuit.

22. A detector as in claim 18, wherein said step of applying a negative pressure includes changing a volume of a portion of said fluid circuit.

23. A detector as in claim 18, wherein said step of detecting includes detecting air bubbles in fluid.

24. A detector as in claim 18, wherein:

said step of applying includes reversing a direction of flow of fluid in said fluid circuit;

said step of detecting includes detecting air with an air sensor located to detect air at a specified position in said fluid circuit; and a duration of said second time is at least long as required to cause said fluid to flow from a terminus of said fluid circuit to said specified position.

25. A tubing set for a leak detecting blood treatment device, comprising:

draw and return lines connectable to at least one access of a patient for the draft and return of blood;

at least a body of a four-way valve with four ports, at least two of which are sealingly connected to said draw and return lines respectively;

arterial and venous lines connectable to a blood processing machine, said arterial and venous lines being connected, respectively, to two others of said four ports.

26. A leak detection device connectable to a fluid infusion or treatment system, comprising:

a support for a fluid circuit configured to convey fluid between a source and an outlet for connection to a patient;

at least an actuator operative to control a portion of said fluid circuit such that a negative pressure can be selectively generated in an outlet portion of said fluid circuit at selected times;

a controller connected to control said actuator and configured to generate a negative pressure in said outlet portion automatically and repeatedly during the course of a treatment of said patient such that a predefined volume of fluid is displaced in a reverse direction;

said controller being further configured to control said actuator such that, at other times, a positive pressure is permitted in said outlet portion.

27. A device as in claim 26, wherein said actuator is configured to control a four-way valve portion of said fluid circuit.

28. A device as in claim 27, wherein said fluid is blood.

29. A device as in claim 26, wherein said actuator is configured to control a four-way valve portion of said fluid circuit that changes a direction of flow in said portion of said fluid circuit and at least another portion of said fluid circuit such that a continuous reverse flow between said patient and said outlet portion is generated when said negative pressure is generated.

30. A device as in claim 29, wherein said fluid is blood.

31. A device as in claim 26, wherein said fluid is blood.

32. A device as in claim 26, wherein:

said source includes an air sensor and a source fluid circuit leading to said air sensor, said source fluid circuit being one of connected and connectable to said source;

said controller is configured such that said predefined volume of fluid is sufficient to insure that air infiltrating at said terminus of said outlet portion reaches a point of detectablility by said air sensor.

33. A device as in claim 32, wherein said fluid is blood.

34. A device as in claim 26, wherein said controller is configured such that said negative pressure in said outlet portion is generated with such regularity that no more than a predetermined volume of said fluid is conveyed through said outlet portion before said negative pressure is again generated.

35. A device as in claim 34, wherein said fluid is blood.

36. A device as in claim 26, further comprising an air sensor positioned to detect air in said fluid circuit when said fluid flows in reverse responsively to said controller.

37. A device as in claim 36, wherein said fluid is blood.

38. A device as in claim 36, wherein said controller is configured such that said predefined volume of fluid is sufficient to insure that air infiltrating at said terminus of said outlet portion reaches a point of being detectable by said air sensor.

39. A device as in claim 38, wherein said fluid is blood.

40. A device as in claim 38, further comprising at least one of a fluid flow halting actuator configured to halt flow in said fluid circuit and an alarm, said controller being configured to actuate said at least one a of a fluid flow halting actuator configured to halt flow in said fluid circuit and an alarm responsively to a signal from said air sensor.

41. A device as in claim 40, wherein said fluid is blood.

42. A leak detector comprising:
a controller configured to detect a leak in a fluid infusion or treatment system that includes a source of fluid to be pumped into a patient;
the controller drawing from said source and conveying said fluid from said source to said patient during a first time and automatically regularly generating a negative pressure such that said fluid is drawn in a reverse direction away from said patient creating a reverse flow of said fluid and one detecting a presence and a flow of air into said fluid infusion system.

43. A detector as in claim 42, further comprising a sensor connected to said controller to detect a presence of air in said reverse flow.

44. A detector as in claim 42, wherein said fluid includes blood.

45. A detector as in claim 42 wherein said controller is configured to one of generate an alarm signal and halt a flow of fluid responsively to detecting said one of a presence and a flow.

46. A detector as in claim 45, wherein said fluid is blood.

47. A detector as in claim 42, wherein said controller generates said negative pressure by controlling a flow reversing actuator.

48. A detector as in claim 47, wherein said fluid is blood.

49. A detector as in claim 42, wherein said source of fluid is said patient's blood supply and said reverse flow is such that blood is drawn from said patient.

50. A detector as in claim 42, wherein each instance of said reverse flow results in a displacement of said fluid sufficient to transport air infiltrating a supply access to said patient to point of detectability by a nearest air sensor to said patient.

51. A detector as in claim 50, wherein said fluid is blood.

52. A detector as in claim 42, wherein said negative pressure is generated with such regularity that no more than a predetermined volume of said fluid is conveyed to said patient before said negative pressure is again generated.

53. A detector as in claim 52, wherein said fluid is blood.

54. A leak detector for a sterile contiguous fluid line for infusing a patient, the fluid line including a draw line connectable to at least one patient access and a return line connectable to said at least one patient access, said detector comprising:
a portion adapted to be interoperable with a pump actuator such that fluid may be conveyed therethrough;
a filter, or filter connectors to permit connection to a filter, to complete a closed fluid circuit joining said draw and return lines;
at least a wetted portion of a device configured to generate a negative pressure in said return line, whereby a flow through said return line may be reversed.

55. A detector line as in claim 54, wherein said device configured to generate a negative pressure is further configured to reverse a flow in both said return line and said draw line.

56. A detector as in claim 54, wherein said device configured to generate a negative pressure in said return line includes at least a portion of a four-way valve.

57. A leak detecting replacement kit for infusing a patient, the replacement kit including a blood line with a draw line connectable to at least one patient blood access, a return line connectable to said at least one patient blood access, a portion adapted to be interoperable with a pump actuator such that fluid may be conveyed therethrough, a filter, or filter connectors to permit connection to a filter, to complete a closed fluid circuit joining said draw and return lines; instructions for using said blood line providing for the installation of said adapted to be interoperable with a pump actuator into a location such that it becomes interoperable with a reversible pump.

58. A leak detecting replacement kit for infusing a patient, comprising:
a blood line including:
a draw line connectable to at least one patient blood access;
a return line connectable to said at least one patient blood access;
a portion adapted to be interoperable with a flow reversing actuator;
a filter, or filter connectors to permit connection to a filter, to complete a closed fluid circuit joining said draw and return lines;
instructions for using said blood line providing for the installation of said portion adapted to be interoperable with flow reversing actuator into a device with a flow reversing actuator.

59. A kit as in claim 58, wherein said portion adapted to be interoperable with a flow reversing actuator is a wetted portion of a four-way valve.

60. A leak detector for an infusion device for delivering a fluid to a patient, the device including a circuit including a pump, a source end and a delivery end joined by said pump, comprising:
a mechanism to reverse flow at least at said delivery end;
an air detector in said circuit;
said mechanism being controlled such that said mechanism is actuated to reverse said flow automatically and regularly and, at each instance of reversing said flow, to displace enough fluid to transport air infiltrating said circuit at said delivery end to said air detector.

61. A detector as in claim 60, wherein said mechanism is a drive configured to reverse said pump.

62. A leak detector with at least one actuator and a controller programmed to implement a method of detecting a loss of integrity in a liquid circuit, comprising the steps of:

conveying liquid through a circuit during first time;
said step of conveying including applying a positive gauge pressure to said circuit;
regularly applying a negative pressure to said circuit during second time;
detecting a presence of air in said liquid circuit during at least a portion of said second time or after said second time, such that air infiltrating said circuit during said second time, as a result of said negative pressure and a presence of a leak, is detected.

63. A detector as in claim 62, further comprising waiting for the passage of a predetermined volume of liquid through said circuit prior to applying said negative pressure.

64. A detector as in claim 62, wherein the step of applying a negative pressure includes reversing a direction of flow of liquid in said circuit.

65. A detector as in claim 62, wherein said step of applying a negative pressure includes switching a valve to cause liquid to flow in a reverse direction through said circuit.

66. A detector as in claim 62, wherein said step of applying a negative pressure includes changing a volume of a portion of said circuit.

67. A detector as in claim 62, wherein said step of detecting includes detecting air bubbles.

68. A detector as in claim 62, wherein said step of detecting includes detecting air bubbles with an ultrasonic sensor.

69. A detector as in claim 62, wherein:
said step of applying includes reversing a direction of flow of liquid in said circuit;
said step of detecting includes detecting air with an air sensor located to detect air at a specified position in said circuit; and
a duration of said second time at least long enough to cause liquid to flow from a terminus of said circuit to said specified position, whereby leakage of liquid from any point in said circuit between said specified position and said terminus is assured.

70. A leak detector for an infusion device that includes a circuit connectable to a patient to deliver fluid to a patient, comprising:
a reversible conveyance connected to move fluid through said circuit;
an air detector in said circuit;
a controller configured to reverse said conveyance regularly and periodically to draw air into any leaks in said circuit and move said air to said air detector, whereby a leak in said circuit may be detected.

71. A device as in claim 70, wherein said controller is configured to reverse said conveyance such that a volume of fluid sufficient to insure detection of infiltration of air by said air detector.

72. A detector as in claim 70, wherein said conveyance has a four-way valve and is configured to reverse by switching said four-way valve.

73. A detector as in claim 70, wherein said air detector detects air bubbles in said fluid.

74. A detector as in claim 70, wherein said air detector detects air bubbles in said fluid using an acoustical signal.

75. A leak detector for a blood processing machine with a draw circuit and a return circuit connected, respectively, to supply blood from a patient to, and return blood to said patient from, a blood processing device, comprising:
a reversible conveyance connected in said draw and return circuits to drive blood therethrough;
a controller connected to control said reversible conveyance such that said reversible conveyance is regularly reversed each time a predefined volume of blood is passed through said return circuit;
at least one air sensor in at least one of said draw and return circuits;
said controller being configured such that a volume of blood displaced in reverse each time said reversible conveyance is reversed, is at least sufficient to transport fluid from a terminal end of said return circuit up to a point of being detectable by said at least one air sensor.

76. A leak detector as in claim 75, wherein said air sensor detects bubbles in blood.

77. A leak detector as in claim 75, wherein said air sensor is an ultrasonic air sensor.

78. A leak detector as in claim 75, wherein said reversible conveyance includes a four-way valve and a pump.

79. A leak detector as in claim 75, wherein said reversible conveyance includes a reversible pump.

80. A leak detector as in claim 75, wherein said predefined volume is a maximum safe volume of blood said patient may lose due to leaks in said leak detector.

81. A leak detector for a blood processing machine that includes a draw circuit and a return circuit connected, respectively, to supply blood from a patient to, and return blood to said patient from, a blood processing device, comprising:
a reversible conveyance connected in said draw and return circuits to drive blood therethrough;
a controller connected to control said reversible conveyance such that said reversible conveyance is regularly reversed;
at least one air sensor in said circuit;
said controller being configured such that a volume of blood displaced in reverse each time said reversible conveyance is reversed is sufficient to insure blood from a terminal end of said return circuit is drawn at least to said at least one air sensor.

82. A leak detector as in claim 81, wherein said air sensor detects bubbles in blood.

83. A leak detector as in claim 81, wherein said air sensor is an ultrasonic air sensor.

84. A leak detector as in claim 81, wherein said reversible conveyance includes a four-way valve and a pump.

85. A leak detector as in claim 81, wherein said reversible conveyance includes a reversible pump.

86. A device for detecting leaks and connectable to a blood processing system having an air sensor adapted to detect blood in a blood circuit, said blood circuit having draw and return lines:
a conduit connectable to said return line;
a fluid conveyance connectable to said return line and said conduit and configured to connect said return line to a patient return access;
said conveyance being adapted to selectively and generate a reverse flow in said conduit and convey said reverse flow to said draw line;

a final control configured to control said conveyance to generate said reverse flow repeatedly during a treatment cycle of said blood processing leak detector.

87. A leak detector for a blood processing machine that includes an access blood circuit connectable to a patient to remove blood from, and deliver blood to, said patient and a a process blood circuit including a treatment component adapted to treat blood circulated through said process blood circuit, comprising:

a conveyance connected to move blood through said process and access blood circuits configured to generate a negative pressure in a return portion of said access blood circuit;

an detector configured to detect infiltration of air in said return portion;

a controller configured to generate said negative pressure in said conveyance repeatedly during a treatment cycle to draw air into said access circuit.

88. A detector as in claim 87, wherein said detector includes an acoustic sensor configured to detect an audio signature of air infiltrating a said portion.

89. A detector as in claim 88, wherein said sensor is a hydrophone.

* * * * *

UNITED STATES PATENT AND TRADEMARK OFFICE
CERTIFICATE OF CORRECTION

PATENT NO. : 6,572,576 B2  Page 1 of 1
DATED : June 3, 2003
INVENTOR(S) : Brugger et al.

It is certified that error appears in the above-identified patent and that said Letters Patent is hereby corrected as shown below:

<u>Title page,</u>
Item [56], U.S. PATENT DOCUMENTS, please insert the following references:
```
-- 6,044,691 A    4/2001      Kenley, et al.
   5,830,365 A    11/1998     Schneditz
   6,189,388 A    2/2001      Cole et al.
   5,178,763 A    1/1993      Delaunay
   3,985,134 A    10/1976     Lissot
   6,221,040 A    4/2001      Kleinekofort
   5,120,303 A    6/1992      Hombroucks
   5,605,630 A    2/1997      Shibata
   5,011,607 A    4/1991      Shinzato
   5,468,390 A    11/1995     Crivello, et al.
   4,181,610 A    1/1980      Shintani, et al.
   4,324,662 A    4/1982      Schnell
   4,885,087 A    12/1989     Kopf
   4,468,866 A    3/1987      Malbrancq, et al.
   6,090,048 A    10/1998     Hertz, et al.
   5,817,043 A    10/1998     Utterberg
   5,894,011 A    4/1999      Prosl, et al.
   6,177,049 A    1/2001      Schnell, et al. --
```
Please insert the following immediately before OTHER PUBICATIONS
-- FOREIGN PATENT DOCUMENTS
99/24145    9/11/1998    England --

Signed and Sealed this

Twentieth Day of January, 2004

JON W. DUDAS
*Acting Director of the United States Patent and Trademark Office*